United States Patent
Acedo et al.

(10) Patent No.: US 12,161,059 B2
(45) Date of Patent: Dec. 10, 2024

(54) METHODS AND SYSTEMS FOR ASSESSING AGRICULTURE PRACTICES AND INPUTS WITH TIME AND LOCATION FACTORS

(71) Applicant: Biome Makers Inc., West Sacramento, CA (US)

(72) Inventors: Alberto Acedo, Castile and León (ES); Nabeel Imam, Santiago (CL); Felipe Engelberger, Santiago (CL); Ariel Romeo-Cares, Luján de Cuyo (AR); Héctor Ortega-Arranz, Valladolid (ES); Eneas Marin, Valladolid (ES); Daniel Almonacid, San Diego, CA (US); Adrian Ferrero, La Bañeza (ES); Beatriz Garcia-Jimenez, Madrid (ES); Lisa Röttjers, Eygelshoven (NL)

(73) Assignee: Biome Makers Inc., Davis, CA (US)

( * ) Notice: Subject to any disclaimer, the term of this patent is extended or adjusted under 35 U.S.C. 154(b) by 352 days.

(21) Appl. No.: 17/703,095

(22) Filed: Mar. 24, 2022

(65) Prior Publication Data
US 2022/0312661 A1 Oct. 6, 2022

Related U.S. Application Data

(60) Provisional application No. 63/169,131, filed on Mar. 31, 2021.

(51) Int. Cl.
| | | |
|---|---|---|
| G06F 11/30 | (2006.01) | |
| A01B 79/00 | (2006.01) | |
| A01B 79/02 | (2006.01) | |
| C12Q 1/689 | (2018.01) | |
| C12Q 1/6895 | (2018.01) | |
| G16B 10/00 | (2019.01) | |
| G16B 40/00 | (2019.01) | |

(52) U.S. Cl.
CPC ............ *A01B 79/005* (2013.01); *A01B 79/02* (2013.01); *C12Q 1/689* (2013.01); *C12Q 1/6895* (2013.01); *G16B 10/00* (2019.02); *G16B 40/00* (2019.02)

(58) Field of Classification Search
CPC .................................................... A01B 79/005
See application file for complete search history.

(56) References Cited

U.S. PATENT DOCUMENTS 8,906,668 B2   12/2014   Henn et al.
9,771,795 B2    9/2017   Knight et al.
(Continued)

OTHER PUBLICATIONS

PCT/US2022/21663 Written Opinion May 24, 2022 (Year: 2022).*
(Continued)

*Primary Examiner* — Phuong Huynh

(57) ABSTRACT

The invention(s) include systems and methods for receiving and processing agriculture-associated samples with sample processing architecture structured to rapidly return outputs characterizing effects of agriculture inputs and practices over time. Control instructions based upon outputs of the systems and methods are then executed for maintaining or improving performance of crops and agriculture sites (e.g., in relation to yield, in relation to nutrient characteristics) in a sustainable manner (e.g., environmentally sustainable manner). System and method outputs can further be used to affect modifications to product treatments generated by associated manufacturers.

18 Claims, 16 Drawing Sheets

(56) References Cited

U.S. PATENT DOCUMENTS

| | | |
|---|---|---|
| 10,347,362 B2 | 7/2019 | Apte et al. |
| 10,395,355 B2 | 8/2019 | Cohen |
| 10,827,669 B2 | 11/2020 | Xu et al. |
| 11,028,449 B2 | 6/2021 | Knight et al. |
| 2002/0103688 A1 | 8/2002 | Schneider |
| 2005/0234691 A1 | 10/2005 | Singh et al. |
| 2011/0137456 A1 | 6/2011 | Koselka et al. |
| 2012/0109614 A1 | 5/2012 | Lindores |
| 2014/0109249 A1 | 4/2014 | Turner et al. |
| 2014/0120063 A1 | 5/2014 | Sonnenburg |
| 2015/0185196 A1 | 7/2015 | Coram et al. |
| 2016/0217230 A1 | 7/2016 | Mewes et al. |
| 2016/0290132 A1 | 10/2016 | Knight et al. |
| 2016/0290918 A1 | 10/2016 | Xu et al. |
| 2018/0213800 A1 | 8/2018 | Djonovic et al. |
| 2018/0363031 A1* | 12/2018 | Becares ............... G16B 40/00 |
| 2020/0194126 A1 | 6/2020 | Lim et al. |
| 2020/0271636 A1 | 8/2020 | Hartman et al. |
| 2021/0009483 A1 | 1/2021 | Temme et al. |
| 2021/0010993 A1* | 1/2021 | Shibata ............... G01N 33/24 |
| 2021/0092933 A1 | 4/2021 | Spangenberg et al. |

OTHER PUBLICATIONS

Schmidt et al. "Agricultural management and plant selection interactively affect rhizosphere microbial community structure and nitrogen cycling", Microbiome vol. 7, Article No. 146, Jul. 11, 2019. Retrieved on Jul. 2, 2021. USA.

Girvan et al. "Community structure in social and biological networks", PNAS vol. 99, issue 12, Jun. 11, 2002. USA.

Van Klompenburg et al. "Crop yield prediction using machine learning: A systematic literature review", Computers and Electronics in Agriculture. 177(2020)105709, Aug. 18, 2020.

Konopka, Allan. "What is microbial community ecology", The ISME Journal. (2009) 3, 1223-1230. Aug. 6, 2009.

Netz et al. "Estimating computational limits on theoretical descriptions of biological cells", PNAS vol. 118, issue 6, Jan. 25, 2021. USA.

Veech, Joseph A. "A probablistic model for analysing species co-occurrence", Global Ecology and Biogeography, 2012.

Watts, et al. "Collective dynamics of 'small-world' networks". Nature vol. 393. Jun. 4, 1998.

Zele et al. "Ecology and evolution of facilitation among symbionts". Nature Communications (2018)9:4869.

Ortiz-Alvarez, et al. "Network Properties of Local Fungal Communities Reveal the Anthropogenic Disturbance Consequences of Farming Practices in Vineyard Soils". mSystems (2021)6;3.

Clauset, et al. "Finding community structure in very large networks". Physical Review (2004)70:066111.

McMurdie, et al. "phyloseq: An R Package for Reproducible Interactive Analysis and Graphics of Microbiome Census Data". PLOS One (2013)8:4.

* cited by examiner

|  | t1-t0 | Q | t2-t0 | Q | t3-t0 | Q |
|---|---|---|---|---|---|---|
| Carbon Cycle | 166.36 | 0.01 | -10.97 | 0.69 | 8.44 | N/A |
| Carbon Fixation | 7.13 | 0.67 | -31.65 | 0.07 | -20.39 | 0.28 |
| Fermentation | 54.44 | 0.05 | -3 | N/A | 5.9 | N/A |
| Organic Matter Release | 38.68 | 0 | 2.32 | N/A | 8 | 0.49 |
| Aerobic Respiration | -5.68 | 0.56 | 17.8 | 0.13 | 9.81 | 0.38 |
| Methanogenesis | -23.3 | 0.33 | -40.78 | 0.06 | -31.85 | 0.17 |
|  |  |  |  |  |  |  |
| Nitrogen Cycle | -9.36 | N/A | 105.36 | 0.15 | 60.67 | 0.34 |
| Inorganic Cycle Health | -15.02 | 0.46 | -7.23 | 0.67 | -17.01 | 0.41 |
| Organic Nitrogen Formation | 21.22 | 0.11 | -19.43 | 0.07 | -8.87 | 0.45 |
| Organic Nitrogen Degradation | 17 | 0.16 | 4.65 | 0.64 | 8.36 | 0.48 |

|  | t1-t0 | Q | t2-t0 | Q | t3-t0 | Q |
|---|---|---|---|---|---|---|
| Phosphorous Pathways | 99.92 | 0.18 | 40.1 | 0.51 | 25.81 | 0.62 |
| Inorganic P Assimilation | -12.87 | 0 | 1.46 | N/A | -3.2 | 0.43 |
| Organic P Assimilation | 0.7 | N/A | -8.43 | 0.06 | -4.41 | 0.35 |
| P Solubilization | 32.77 | 0.52 | 25.43 | 0.63 | 12.11 | N/A |
|  |  |  |  |  |  |  |
| Potassium Pathways | 41.47 | 0.53 | 45.77 | 0.49 | 13.18 | N/A |
| Potassium Uptake | 12.24 | 0 | 2.43 | 0.56 | 4.7 | 0.29 |
| Potassium Solubilization | 32.77 | 0.52 | 25.43 | 0.63 | 12.11 | N/A |

FIGURE 4A

|  | t1-t0 | Q | t2-t0 | Q | t3-t0 | Q |
|---|---|---|---|---|---|---|
| Iron Assimilation | 357.11 | 0 | 24.79 | 0.63 | 68.96 | 0.32 |
| Zinc Transport Equilibrium | 102.69 | 0.04 | -41.63 | 0.13 | -3.34 | N/A |
| Manganese Transport Equilibrium | -37.75 | 0.21 | 47.18 | 0.31 | 5.16 | N/A |
| Sulfur Cycle Equilibrium | 414.82 | 0.11 | 309.35 | 0.17 | 258.09 | 0.22 |
| Calcium Transport | 18.43 | 0.06 | -15.58 | 0.07 | -5.76 | 0.52 |
| Copper Transport | 19.12 | 0.14 | -17.2 | 0.12 | -7.36 | 0.52 |
| Chlorine Transport | 75.9 | 0.01 | -1.29 | N/A | 4.24 | N/A |
| Magnesium Uptake | -8.23 | 0.29 | 4.17 | 0.61 | -3.7 | 0.61 |

FIGURE 4B

|  | t1-t0 | Q | t2-t0 | Q | t3-t0 | Q |
|---|---|---|---|---|---|---|
| Phytohormone Evolution | -16.6 | 0.63 | -42.24 | 0.21 | -61.17 | 0.03 |
| Cytokinin Production | 92.89 | 0.16 | -54.55 | 0.1 | -65.98 | 0.02 |
| Auxin Production | 19.62 | 0.58 | -24.1 | 0.43 | -40.1 | 0.16 |
| Gibberellin Production | -66.84 | 0.23 | -67.19 | 0.22 | -85.99 | 0.05 |
| Stress Adaptors Evolution | 54.02 | 0.17 | -24.45 | 0.36 | -37.74 | 0.13 |
| ACC Deaminase | 79.97 | 0.11 | -20.24 | 0.49 | 19.7 | 0.57 |
| EPS Production | 4.05 | N/A | 7.83 | N/A | -35.23 | 0.22 |
| Heavy Metal Solubilization | 59.89 | 0.33 | 11.55 | N/A | -34.27 | 0.38 |
| Salt Tolerance | 123.08 | 0.09 | -55.93 | 0.09 | -30.99 | 0.4 |
| Siderophore Production | 74.07 | 0.23 | -29.11 | 0.46 | -38.2 | 0.3 |
| Salicylic Acid | -45.16 | 0.64 | -95.22 | 0.34 | -90.76 | 0.17 |
| Abscisic Acid | 208.22 | 0.2 | -74.29 | 0.12 | -93.74 | 0 |

|  | t1-t0 | Q | t2-t0 | Q | t3-t0 | Q |
|---|---|---|---|---|---|---|
| Biocontrol | 776.3 | 0.17 | -11.03 | N/A | -18.79 | N/A |
| Fungicide Agents | -71.77 | 0.47 | -72.29 | 0.47 | -98.86 | 0.02 |
| Insecticide Agents | 1387.99 | 0.11 | 12.58 | N/A | 823.53 | 0.17 |
| Nematicide Agents | 545.36 | 0.43 | 77.39 | N/A | -90.08 | 0.34 |
| Bactericide Agents | N/A | N/A | N/A | N/A | N/A | N/A |

FIGURE 4C

| | t1-t0 | Q | t2-t0 | Q | t3-t0 | Q |
|---|---|---|---|---|---|---|
| Albinism | -99.33 | 0.19 | 237.16 | N/A | -68.31 | N/A |
| Alternaria brown spot | -99.59 | 0.27 | 58.22 | N/A | 28.17 | N/A |
| Alternaria rot | -59.71 | 0.65 | -41.55 | N/A | -84.6 | 0.43 |
| Anthracnose | -71.22 | 0.54 | -70.27 | N/A | -98.98 | 0.06 |
| Black mold rot | -9.46 | N/A | 95.82 | N/A | 100.04 | N/A |
| Botrytis blossom and twig blight | -96.13 | N/A | 380.34 | N/A | 383.33 | N/A |
| Charcoal root rot | -99.94 | 0.06 | 30.28 | N/A | 35.19 | N/A |
| Damping-off | -2.86 | N/A | -1.81 | N/A | -1.06 | N/A |
| Diplodia stem-end rot | -97.92 | 0.15 | -98.87 | 0.21 | -83.84 | 0.43 |
| Fusarium rot | -63.83 | 0.43 | -80.68 | 0.21 | -1.73 | N/A |
| Fusarium wilt | -99.93 | 0.15 | -99.89 | 0.23 | -99.18 | 0.26 |
| Gray mold (Botrytis) | -96.13 | N/A | 380.34 | N/A | 383.33 | N/A |

| | t1-t0 | Q | t2-t0 | Q | t3-t0 | Q |
|---|---|---|---|---|---|---|
| Greasy spot | 1005.32 | N/A | 1112.08 | N/A | 1132.01 | N/A |
| Green mold | -87.24 | N/A | -97.32 | N/A | -97.38 | N/A |
| Mucor fruit rot | -97.01 | N/A | -4.95 | N/A | -91.44 | N/A |
| Pink mold | -4902 | N/A | -99.18 | 0.23 | -20.53 | N/A |
| Pleospora rot | -100 | 0.09 | -97.64 | N/A | -99.99 | 0.1 |
| Poria root rot | 43719.6 | 0.09 | 14273.4 | 0.12 | 201.95 | 0.56 |
| Postbloom fruit drop | -71.22 | 0.54 | -70.27 | N/A | -98.98 | 0.06 |
| Rio Grande gummosis | -97.92 | 0.15 | -98.87 | 0.21 | -83.84 | 0.43 |
| Rootlet rot | -2.86 | N/A | -1.81 | N/A | -1.06 | N/A |
| White wood rot | -82.68 | N/A | 11.35 | N/A | 4.49 | N/A |

FIGURE 4D

METHODS AND SYSTEMS FOR ASSESSING AGRICULTURE PRACTICES AND INPUTS WITH TIME AND LOCATION FACTORS

CROSS-REFERENCE TO RELATED APPLICATIONS

This application claims the benefit of U.S. Provisional Application No. 63/169,131 filed on Mar. 31, 2021, which is incorporated in its entirety herein by this reference.

TECHNICAL FIELD

The disclosure generally relates to tools and systems executing methods for sampling and characterizing effects of practices and inputs on agricultural sites and crops, with actionable outcomes.

BACKGROUND

Agriculture ecosystems are human-managed ecosystems subject to various ecological inputs, in relation to steady state scenarios and in response to various perturbations. Understanding the changes in soil microbial communities is a fruitful way to improve management practices, test various products and/or other agricultural inputs, evaluate sustainability, and therefore improve agriculture site productivity.

However, current implementations for assessing states of agriculture sites in relation to various inputs, as well as tracking states of agriculture sites longitudinally, are severely limited. Furthermore, current methods for characterizing health states of agriculture sites and effects of inputs are subject to errors (e.g., false positive errors, other errors), due to poor performance of architecture for processing samples and data from agriculture sites.

Acquisition and processing of the appropriate data from agriculture-associated samples at one or more time points and/or one or more locations, development of highly accurate and efficient models for characterization of ecosystem statuses, and generation of outputs and implementation of actions for maintaining such ecosystems, improving yields, improving crop nutrient content, improving soil carbon sequestration characteristics, identifying soil nutrient status and/or identifying disease risk are all areas of innovation in which the inventions described herein provide value.

BRIEF DESCRIPTION OF THE FIGURES

FIGS. 4A through 4D depict example outputs related to changes in major nutrient evolution, minor nutrient evolution, plant growth promoters, biocontrol agents, and disease risk across locations and time points with respect to treatments and controls, in accordance with methods and systems for assessing agriculture practices and inputs.

DESCRIPTION OF THE EMBODIMENTS

Figure 1A:
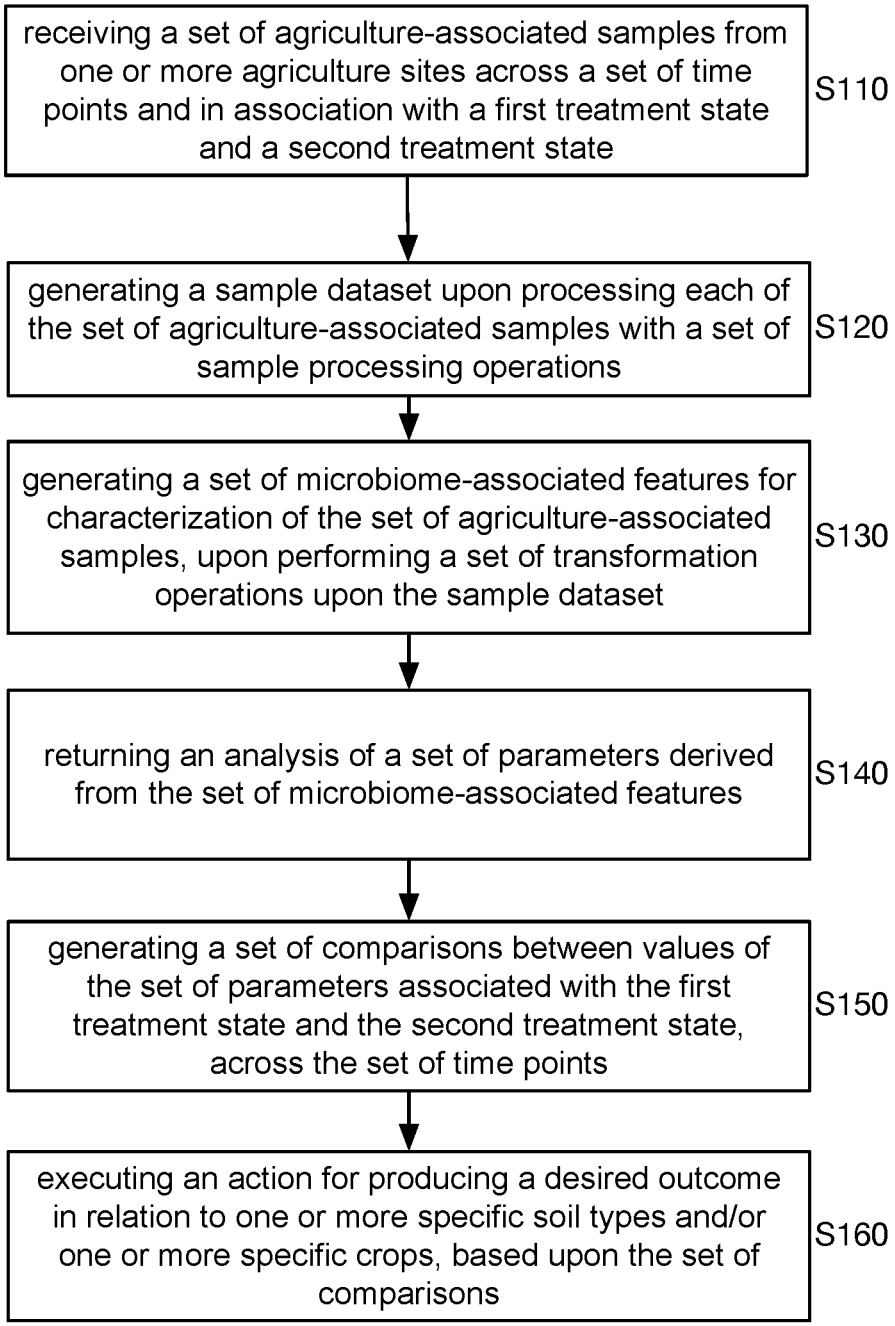
FIG. 1A depicts an embodiment of a workflow of a method for assessing agriculture practices and inputs.

While various embodiments of the invention have been shown and described herein, it will be obvious to those skilled in the art that such embodiments are provided by way of example only. Numerous variations, changes, and substitutions can occur to those skilled in the art without departing from the invention. It should be understood that various alternatives to the embodiments of the invention described herein can be employed.

1. Benefit(s)

The invention(s) provide systems and methods for assessment of management practices or agriculture inputs in samples. Assessment can be conducted in relation to prediction of various agriculture site and crop features, which are useful in downstream applications in relation to recommending, implementing changes to, or maintaining various agriculture inputs and/or management practices to improve productivity or maintain health of the agriculture site. Over 15% of farm production costs are attributed to fertilizers and crop-protection inputs, and additional costs are attributed to various management practices. The invention(s) thus provide a way to assess effectiveness of such inputs and modify application of inputs and other practices to improve states, productivity, and environmental sustainability of production.

In examples, the inventions(s) thus involve systems and methods that assess the effect of management practices or agricultural inputs in sample biology over time and across locations, in order to assess changes in various treatments (e.g., different treatments, treatments vs. controls, etc.) to determine comparative measures (e.g., d(Treatment at Tn-T0)/d(Control at Tn-T0)). Such methods involve novel nucleic acid sequencing processes and processing of samples for characterization of other targets associated with microbiome communities and nutrients associated with agriculture sites, where, in examples, factors characterized can include taxonomic indices/biodiversity features, functional features/nutrient bioactivity, and/or, and/or ecological indices health statuses.

Such insights can further provide growers/agriculture site managers/agriculture site apparatuses with actionable instructions (e.g., computer-implemented instructions) for selecting one or more inputs for producing a desired result.

Such insights can further provide manufacturers of product inputs (e.g., bioinnoculants, stimulants, etc.) with actionable instructions for improving products and/or targeting various customers based upon performance characteristics in relation to specific crops and soil types.

In specific examples, the invention(s) can be used to measure the effects of crop inputs in order to generate functional claims from various trials, with respect to food security, yield improvements, quality improvements, environmental awareness, sustainability (e.g., with respect to carbon sequestration), and/or other benefits.

In variations, the invention(s) process samples to assess soil microbiome features, in order to assess microbiome-derived characteristics related to nutrient availability for crops, pathogen control, defense mechanisms, resistance, resilience, and/or other features. Such soil microbiome features (e.g., associated with bacteria, fungi, viruses, etc.) can be monitored in relation to application of various products (e.g., agriculture inputs) and management practices, in order to assess or guide application of products that can be used to promote presence and activity of beneficial microbial species, restore microorganism communities, and serve other suitable functions. Analyses provided by the invention(s) can characterize the general effects of treatment application on composition and structure of the soil microbiota (e.g., taxonomic biodiversity level, community resistance/resilience, etc.), as well as specific effects of treatment on abundance and distribution of microbial functional groups as well as co-relations with complementary metadata. Such approaches enable identification of relevant microbial species or groups to answer agronomical-relevant questions. Example outputs of the invention(s) include analyses regarding: 1) impact of products/inputs/practices upon biodiversity level (e.g., richness and evenness of microbial species) at an agriculture site; 2) effects of products/inputs/practices upon nutrition-related bioactivity of soil at the agriculture site; 3) effects of products/inputs/practices on crop health statuses; and 4) products/inputs/practices ratings.

Additionally, in embodiments, the invention(s) described implement rapid processing of samples and data generated from sample processing, in order to extract insights related to predicted features of crops and agriculture sites, in a manner that cannot be practically performed by the human mind.

Additionally, in embodiments, the invention(s) provide methods for determining microbiome-associated or -derived properties and/or properties derived from network properties in local microbial, fungal, and/or other organism communities, and to use them to assess the impact of different agricultural inputs and/or practices (e.g., agricultural management practices) over time. Impact can be determined in relation to biosustainability, crop health improvement, crop nutritional characteristics, and/or other characteristics. For instance, the invention(s) can further provide methods and systems for evaluating, guiding, and/or executing implementation of various agricultural inputs and/or management practices for enhancement of yield (e.g., in relation to specific soil types and/or for specific crops) and/or improvement of agriculture site characteristics (e.g., with respect to health, with respect to sustainability).

In embodiments, the method(s) promote agro-ecosystem sustainability through assessment of soil organism communities. In particular, the complexity of microbial communities, at both taxonomic and functional levels, is impossible to assess practically without systems and methods described herein, where the methods cannot be practically implemented in the human mind. The invention(s) thus process samples to extract patterns connecting sample microbiome composition with ecosystem function in order to drive interventions based upon the impact of biotic (e.g., interspecies interactions, intraspecies interactions) and abiotic (e.g. climate or anthropogenic disturbances) factors. As such, the invention(s) provide a new methodological framework—inferring emergent properties from local networks—with assessment and guidance of different ecological strategies in agricultural site communities. In practical applications, the methods can be used to restore soil functionality, predict yields, manage crop vulnerabilities, optimize their farming practices, and improve the sustainability (e.g., environmental sustainability, in relation to carbon-associated goals) of agricultural sites. Additionally or alternatively, the inventions can guide or inform management practices in relation to effects on soil carbon sequestration.

Additionally, the inventions apply outputs of the analyses to effect one or more actions (e.g., treatments) to maintain or improve the natural ecological site conditions, thereby providing practical applications of the method(s) and models involved.

Additionally, the inventions involve collection of samples from various agricultural sites, processing of samples to extract data features, application of one or more transformations to the data features to generate modified digital objects, create improved training data sets for machine learning/classification algorithms, and iteratively train the machine learning/classification algorithms, such that agriculture site statuses can be returned upon processing subsequent samples hitherto unseen by the algorithm.

Additionally, in embodiments, the invention(s) described can be used to develop models involving finite sets of physicochemical properties for product testing trials. Additionally or alternatively, models can implement additional properties (e.g., microbiome-derived properties, physicochemical properties, weather, crop type-associated properties, etc.) for generating predictions.

Additionally, the inventions described provide systems and a platform including architecture for agriculture sample extraction and processing, which provide improved tools for monitoring, forecasting, and responding to events (e.g., changes in productivity, events associated with management practices, environmental perturbations, product-induced perturbations, etc.) associated with one or more agricultural sites. Additionally or alternatively, the inventions can assess implementation of a plant variety and/or a seed variety at an agriculture site.

Additionally, the inventions involve collection of samples from various agricultural sites, processing of samples to extract data features, application of one or more transformations to the data features to generate modified digital objects, create appropriate and/or augmented training data sets for machine learning/classification algorithms, and iteratively train the machine learning/classification algorithms, such that agriculture site statuses and future recommendations can be returned upon processing subsequent samples.

In applications, the inventions can contribute to significantly increased yields of major/important crops (e.g., rice, wheat, soybeans, maize, potatoes, etc.) to improve global food production in relation to anticipated world population increases as well as preservation of soil by monitoring microbiome communities. In particular, using potato crops as an example, applications of the inventions can characterize yield (e.g., maximum potential yield) of potato crops based on current inputs and management practices Additionally or alternatively, the invention(s) can confer any other suitable benefit in any crop.

1.1 Definitions

The terms microbiome, microbiome information, microbiome data, microbiome population, microbiome panel and similar terms are used in the broadest possible sense, unless expressly stated otherwise, and would include: a census of currently present microorganisms, both living and non-living, which may have been present months, years, millennia or longer; a census of components of the microbiome other than bacteria and archaea (e.g., viruses, microbial eukaryotes, etc.); population studies and characterizations of microorganisms, genetic material, and biologic material; a census of any detectable biological material; and information that is derived or ascertained from genetic material, biomolecular makeup, fragments of genetic material, DNA, RNA, protein, carbohydrate, metabolite profile, fragment of biological materials and combinations and variations of these.

As used herein, the terms real-time microbiome data or information includes microbiome information that is collected or obtained at a particular setting or stage of an agricultural process for one or more agricultural sites.

As used herein, the terms derived microbiome information and derived microbiome data are to be given their broadest possible meaning, unless specified otherwise, and includes any real-time, microbiome information that has been computationally linked or used to create a relationship.

As used herein, the terms predictive microbiome information and predictive microbiome data are to be given their broadest possible meaning, unless specified otherwise, and includes information that is based upon combinations and computational links or processing of historic, predictive, real-time, and derived microbiome information, data, and combinations, variations and derivatives of these, which information predicts, forecasts, directs, or anticipates a future occurrence, event, state, or condition in the industrial setting, or allows interpretation of a current or past occurrence.

Real time, derived, and predicted data can be collected and stored, and thus, become historic data for ongoing or future decision-making for a process, setting, or application.

"Nucleic acid," "oligonucleotide," and "polynucleotide" refer to deoxyribonucleic acids (DNA) or ribonucleic acids (RNA) and polymers thereof in either single- or double-stranded form. Unless specifically limited, the term encompasses nucleic acids containing known analogues of natural nucleotides that have similar binding properties as the reference nucleic acid and are metabolized in a manner similar to naturally occurring nucleotides. The term nucleic acid is used interchangeably with gene, cDNA, and mRNA encoded by a gene.

The term "microbiome", as used herein, refers to the ecological community of commensal, symbiotic, or pathogenic microorganisms in a sample.

The term "genome" as used herein, refers to the entirety of an organism's hereditary information that is encoded in its primary DNA sequence. The genome includes both the genes and the non-coding sequences. For example, the genome may represent a microbial genome or a mammalian genome.

Reference to "DNA region" should be understood as a reference to a specific section of genomic DNA. These DNA regions are specified either by reference to a gene name or a set of chromosomal coordinates. Both the gene names and the chromosomal coordinates would be well known to, and understood by, the person of skill in the art. In general, a gene can be routinely identified by reference to its name, via which both its sequences and chromosomal location can be routinely obtained, or by reference to its chromosomal coordinates, via which both the gene name and its sequence can also be routinely obtained.

Reference to each of the genes/DNA regions detailed above should be understood as a reference to all forms of these molecules and to fragments or variants thereof. As would be appreciated by the person of skill in the art, some genes are known to exhibit allelic variation or single nucleotide polymorphisms. SNPs encompass insertions and deletions of varying size and simple sequence repeats, such as dinucleotide and trinucleotide repeats. Variants include nucleic acid sequences from the same region sharing at least 90%, 95%, 98%, 99% sequence identity i.e. having one or more deletions, additions, substitutions, inverted sequences etc. relative to the DNA regions described herein. Accordingly, the present invention should be understood to extend to such variants which, in terms of the present applications, achieve the same outcome despite the fact that minor genetic variations between the actual nucleic acid sequences may exist between different bacterial strains. The present invention should therefore be understood to extend to all forms of DNA which arise from any other mutation, polymorphic or allelic variation.

The term "sequencing" as used herein refers to sequencing methods for determining the order of the nucleotide bases-adenine, guanine, cytosine, and thymine—in a nucleic acid molecule (e.g., a DNA or RNA nucleic acid molecule).

The term "barcode" as used herein, refers to any unique, non-naturally occurring, nucleic acid sequence that may be used to identify the originating source of a nucleic acid fragment.

A "computer-readable medium", is an information storage medium that can be accessed by a computer using a commercially available or custom-made interface. Exemplary computer-readable media include memory (e.g., RAM, ROM, flash memory, etc.), optical storage media (e.g., CD-ROM), magnetic storage media (e.g., computer hard drives, floppy disks, etc.), punch cards, or other commercially available media. Information may be transferred between a system of interest and a medium, between computers, or between computers and the computer-readable medium for storage or access of stored information. Such transmission can be electrical, or by other available methods, such as IR links, wireless connections, etc.

Where a range of values is provided, it is understood that each intervening value, between the upper and lower limit of that range and any other stated or intervening value in that stated range is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either both of those included limits are also included in the invention.

Figure 1B:
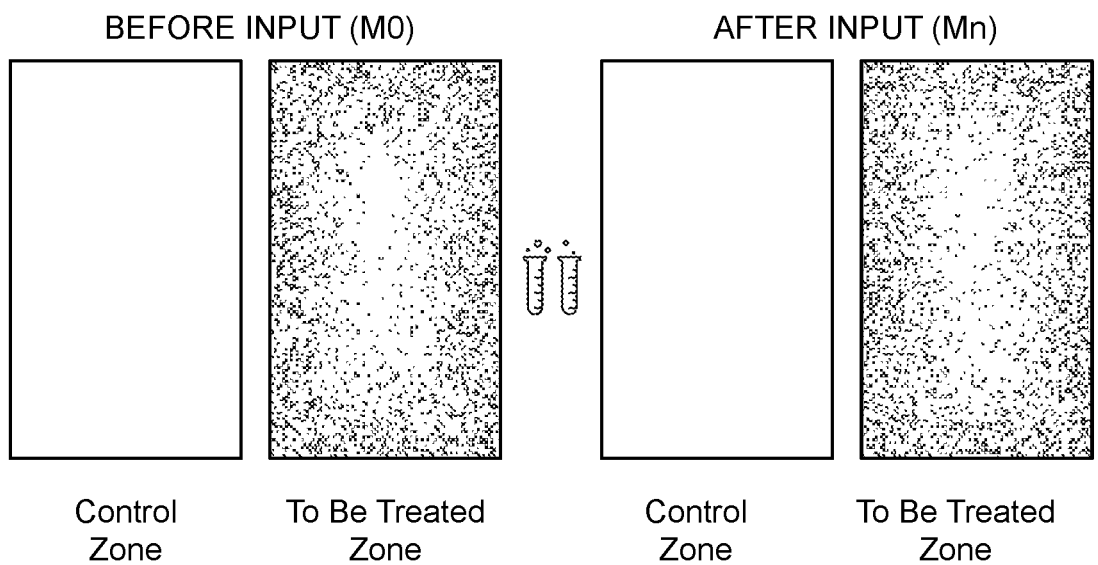
FIG. 1B depicts a schematic of a methodology for assessing agriculture practices and inputs.

2. Method for Assessing Agriculture Inputs and Practices with Longitudinal Characterizations As shown in FIGS. 1A and 1B, an embodiment of a method 100 for assessing agriculture inputs and management practices can include: receiving a set of agriculture-associated samples from one or more agriculture sites across a set of time points and in association with a first treatment state and a second treatment state (e.g., a control state, a different treatment state than the first treatment state) Silo; generating a sample dataset upon processing each of the set of agriculture-associated samples with a set of sample processing operations S120; generating a set of microbiome-associated features for characterization of the set of agriculture-associated samples, upon performing a set of transformation operations upon the sample dataset S130; returning an analysis of a set of parameters derived from the set of microbiome-associated features S140; and generating a set of comparisons between values of the set of parameters associated with the first treatment state and the second treatment state, across the set of time points S150. In some variations, the method 100 can additionally or alternatively include executing an action for producing a desired outcome in relation to one or more specific soil types and/or one or more specific crops, based upon the set of comparisons S160.

The method 100 functions to generate assessments of agriculture sites and inputs/management practices across multiple time points, with multiple samples at one or more locations, with respect to any soil type, and/or with respect to any crop. The method 100 can generate microbiome-associated features (e.g., derived from taxonomic features, functional features, and/or ecological features) for generation of parameters, which can be used to characterize aspects of an agricultural site and/or crops associated with the agricultural site across treatment and control groups. The method 100 implements novel steps for processing samples and data from such samples, in order to improve outcomes and practices. As such, the method 100 can generate insights using processes with improved efficiency and efficacy.

In particular, the method 100 can provide assessments of agriculture sites and evaluation of inputs/practices from samples acquired in as few as two time points, with a limited number of samples. However, assessments and evaluations can be generated from samples taken from more than two time points.

Variations of the methods described can be implemented for various crop types, soil types, agriculture site locations, and/or other factors.

Furthermore, in downstream applications, refinement of models, system architecture, and sample processing techniques can be used to guide testing of, recommendation of, and/or implementation of (e.g., using automated or manual systems/devices) agricultural inputs, products for use, and management practices, in order to improve desired outcomes (e.g., in relation to mitigating disease risk, in relation to yield, in relation to agriculture site health, in relation to sustainability, etc.). As such, the method(s) can provide steps for monitoring, controlling, and analyzing agriculture activities, with practical applications in food production, viticulture, bio-fuel production, and other agricultural activities.

The method(s) described can be implemented by systems and platforms described in Section 3 below. Additionally or alternatively, the method(s) described can be implemented by embodiments, variations, and examples of systems described in U.S. application Ser. No. 17/119,972 filed on 11 Dec. 2020, U.S. application Ser. No. 17/587,016 filed on Jan. 28, 2022, and U.S. application Ser. No. 17/665,332 filed on Feb. 4, 2022, which are each herein incorporated in its entirety by this reference.

2.1 Methods—Sample Reception and Sample Processing

Block S110 recites: receiving a set of agriculture-associated samples from one or more agriculture sites across a set of time points and in association with a first treatment state and a second treatment state; Block S120 recites generating a sample dataset upon processing each of the set of agriculture-associated samples with a set of sample processing operations. Blocks S110 and S120 function to process raw sample material with one or more operations, thereby generating base data from which features can be extracted in subsequent portions of the method.

As shown in FIG. 1B, in relation to the one or more time points, the set of agriculture-associated samples can include multiple samples or a single sample for each time point. In variations, the number of samples can be one sample, two samples, three samples, four samples, five samples, 10 samples, 15 samples, 20 samples, any intermediate number of samples, or greater than 20 samples.

In variations, the set of time points across which samples are acquired and analyzed can include two time points, three time points, four time points, five time points, 10 time points, 15 time points, 20 time points, any intermediate number of time points, or greater than 20 time points. In examples, the method 100 can return results with as few as two time points.

The set of time points can be distributed across time scales on the order of seconds, minutes, hours, days, months, or years; however, the set of time points can additionally or alternatively be distributed across other suitable time scales.

Similarly, the one or more agriculture sites can have any suitable distance relative to each other. Furthermore, the set of agriculture-associated samples can include samples from any soil type and/or in association with any crop. Time points can be prior to treatment, during treatment, and/or after treatment. Time points for biological treatments can be different than those for chemical treatments or other inputs/practices. For instance, time points for biological treatments can be spaced apart by one day, two day, three days, four days, five days, six days, one week, two weeks, three weeks, any intermediate value, or more than three weeks. Time points for chemical treatments can be spaced apart by one week, two weeks, three weeks, four weeks, one month, two months, three months, any intermediate value, or more than three months. Furthermore, variations of Step S110 can implement one time point as a benchmark, in order to assess various management practices/inputs where multiple time points are not needed.

In variations, the treatment states (e.g., first treatment state, second treatment state, third treatment state, control state, etc.) can be associated with a management practice, such as one or more of: organic management practices (e.g., integrating cultural, biological, and mechanical practices that foster cycling of resources, promote ecological balance, and conserve biodiversity without use of synthetic fertilizers, sewage, irradiation, and genetic engineering); non-organic management practices; use of synthetic fertilizers; use of natural fertilizers; biodynamic management practices (e.g., with generation of their own fertility through composting, integrating animals, cover cropping, and crop rotation); conventional management practices (e.g., with standard farming systems, using a variety of synthetic chemical fertilizers, pesticides, herbicides and other continual inputs, etc.).

In variations, the treatment states (e.g., first treatment state, second treatment state, third treatment state, control state, etc.) can be associated with inputs associated with the agriculture site(s) and/or crops from which samples are derived, including one or more of: a biological input including one or more of: a biostimulant, a biofertilizer, a biocontrol agent, a biopesticide, compost, and a biodynamic preparation (wherein the biological input is applied by one or more of: a broadcast spray, an in-furrow spray, seed treatment, application to soil with incorporation, and application to soil without incorporation, etc.); and another suitable input.

In variations, the control state can be associated with an untreated situation in which the samples are acquired from untreated agriculture sites. In variations, the control state can be a baseline treated state for an agriculture site or crop, where the baseline treated state is a suitable reference for changes in treatment state.

Treated and control plots from which samples are acquired can be positioned adjacent to each other at the same agriculture site; alternatively treated and control plots can be otherwise positioned (e.g., not at the same agriculture site).

Samples can be received from various portions of the agriculture site(s) and/or states of processing of crops or other products derived from the agriculture site(s). In embodiments, samples can be extracted from soil, another substrate, water used in agriculture (e.g., water runoff), from various portions of crops, from organisms interacting with crops (e.g., parasites, other symbiotic organisms, etc.), from consumable products (e.g., food, beverages, supplements, etc.) derived from crops, from other surfaces (e.g., conduits used to deliver water or nutrients to crops, etc.), and/or from other suitable sampling sites. The samples can include solid samples (e.g., soil, sediment, rock, food samples). The samples can additionally or alternatively include liquid samples (e.g., surface water, sub-surface water, other liquids derived from crops, consumable products derived from crops, crop-derived products at various stages of processing, fermentation, curing, aging, drying, etc.). The samples can additionally or alternatively include gas samples (e.g., samples from gases obtained from a greenhouse, gases produced during processing of crops or crop-derived products, etc.). Samples can be taken from crop portions (e.g., reproductive portions, petals, leaves, fruits, roots, trunks, flowers, pollen, etc.) and/or from crops in various states of health (e.g., healthy states, distressed states, diseased states, etc.).

Sample volumes can range from 0.01 grams to 1 kilogram (or greater than 1 kilogram, less than 0.01 gram). Additionally or alternatively, sample volumes can range from 1 microliter to 1 liter (or greater than 1 liter, less than 1 microliter).

Samples from different portions of the agriculture site, different portions of a crop, different portions or stages of a product being produces, and/or different sources can be combined in Block Silo.

In relation to Block Silo, sample reception/collection can be performed using equipment (e.g., machinery, robotic apparatus configured to traverse an agricultural site in coordination with retrieval of the set of agriculture samples, other apparatus) and/or manually. In variations, sample reception/collection performed in Step S110 can use any one or more of: an instrument (e.g., scoop for soil, sharp instrument for extracting a portion of a crop specimen, etc.), a permeable substrate (e.g., a swab, a sponge, etc.), a non-permeable substrate (e.g., tape, etc.), a container (e.g., vial, tube, bag, etc.) configured to receive a sample from the agriculture site or associated crops, and any other suitable sample-reception element. In a specific example, samples can be collected from one or more of: soil, other crop-associated solids, water, other crop-associated liquids, gases, and a crop component (e.g., root, stem, leaf, flower, seed, other plant component, etc.). In relation to soil samples, samples can be extracted in relation to a reference point (e.g., distance from surface, distance from plant, etc.). In relation to plant components, samples can be taken from a reference (e.g., distance from leaf, distance, from node, distance along root, etc.). In variations in which multiple samples are taken, samples can be pooled (e.g., combined) or kept distinct.

Furthermore, samples can be received from one or more metacommunities, where a metacommunity is defined as a group of communities within the same habitat/region/pool associated with each agriculture site associated with the set of samples, where the group(s) of communities display multiple possible arrangements according to environmental filters, dispersal restrictions, priority effects and the latter established interactions. As such, features, insights, and actions implemented in subsequent steps of the method can be generated or performed at the metacommunity level and/or at local levels of abstraction.

For variations in which sample numbers are low, Block S110 can include supplementation with a subset of synthetic samples generated based upon latitude and longitude information of an agriculture site (e.g., an agriculture site from which less than a threshold number of samples was acquired). The subset of synthetic samples can be acquired based upon geostatistical models and Markov processes, with architecture for returning sample characteristics without physical sampling, and the method 100 can be subsequently run with a combination of actual and synthetic samples to provide an ecological picture of the unknown soil. All available information can be modeled while missing information can be imputed implicitly with Bayesian models.

In a specific example, samples were acquired from three geographical locations, with respect to a crop (e.g., crops of a citrus grove), with treatment(s) comprising a soil inoculant/soluble yeast/humic acid/humate soil amendment configured to elicit higher populations of and symbiotic communities of various beneficial microbes (e.g., nitrogen-fixing microbes, microbes for solubilization of phosphate into soluble forms of phosphorus, organisms for unlocking of potassium in soil, microbes for solubilization of silicon and other trace minerals, etc.), with two plots per agriculture site (e.g., a first plot as a control, and a second plot associated with the treatment), three time points (e.g., prior to application of the treatment at T0, weeks after initiation of treatment at T1, and months after initiation of treatment at T2), with multiple replicates (e.g., three replicates per plot, time point, geographical location, and crop type). Samples can be collected between 5-8 inches deep, compiling soil from multiple cores within a plot to produced mixed and homogenized soil samples, with cleaning of sampling tools to avoid cross contamination. Samples not shipped immediately should be stored at a desired temperature (e.g., −20 C). Such a design provides high statistical power; however, variations of the specific example can be configured in another suitable manner with respect to location(s), crop(s), treatment(s), plot(s), time point(s), and/or replicate(s). For instance, variations of step S110 can implement between 2 and 10 replicates, or another suitable number of replicates.

In relation to Block S120, processing the set of samples can include wet lab processing techniques (e.g., sample lysis, sample enrichment, sample purification, target material capture or separation, target amplification, etc.), as well as sequencing and library preparation operations. As such, generating sample data in step S120 includes a combination of sample processing techniques (e.g., wet laboratory techniques) and computational techniques (e.g., utilizing tools of bioinformatics) to quantitatively and/or qualitatively characterize the microbiome, functional features, and/or other aspects (e.g., chemistry) of each sample of the agricultural site(s). Sample processing operations can include generation of one or more of: a full metagenomic dataset, a metatranscriptomics dataset, and a proteomics dataset.

As such, in variations, Block S120 can include one or more of: sample pre-processing (e.g., with homogenization or chopping, with use of a buffer, with formation of a pellet, etc.), sample storage (e.g., at appropriate conditions prior to subsequent processing, e.g., at −80 C, at 4 C, at another suitable temperature, etc.); sample lysis (e.g., using physical methods, using chemical methods, using biological methods, etc.); genetic material (e.g., nucleic acid material) extraction including extraction of DNA, RNA, nucleic acid fragments, or other nucleic acid material; protein extraction; nucleic acid purification (e.g., using precipitation, using liquid-liquid based purification, using chromatography, using binding moiety functionalized particles, etc.); target material capture; removal of sample waste; target incubation; target amplification (e.g., using polymerase chain reaction (PCR)-based techniques, using helicase-dependent amplification (HDA), using loop mediated isothermal amplification (LAMP), using self-sustained sequence replication (3SR), using nucleic acid sequence based amplification (NASBA), using strand displacement amplification (SDA), using rolling circle amplification (RCA), ligase chain reaction (LCR), etc.); target enrichment; and/or any other suitable sample processing steps.

In relation to amplification of nucleic acids, primers used can be designed to mitigate amplification bias effects, as well as configured to amplify nucleic acid regions/sequences (e.g., of the 16S region, 18S region, the ITS region, etc.) that are informative taxonomically, phylogenetically, in relation to emergent properties, for formulations, and/or for any other suitable purpose. Primers used in variations of Block S120 can additionally or alternatively include incorporated barcode sequences, unique molecule identifiers, adaptor sequences, or other sequences specific to each sample and/or in association with sequencing platforms, which can facilitate identification of material derived from individual samples post-amplification. Examples of custom primers are described in WO 2017/096385 published Jun. 8, 2017, which is herein incorporated in its entirety by this reference.

Furthermore, sequencing can be performed in coordination with a next generation sequencing platform (e.g., Illumina™ sequencing platform) or other suitable sequencing platform (e.g., nanopore sequencing platform, PacBio platform, MinION platform, etc.). Additionally or alternatively, any other suitable sequencing platform or method can be used (e.g., a Roche 454 Life Sciences platform, a Life Technologies SOLiD platform, etc.). Additionally or alternatively, sample processing can implement any other step configured to facilitate processing (e.g., using a Nextera kit) for performance of a fragmentation operation (e.g., fragmentation and tagging with sequencing adaptors) in cooperation with amplification. Additionally or alternatively, filtering of sequences (e.g., chimeric sequences, other sequences, etc.) can be performed in coordination with Block S120.

In relation to sample acquisition and sequencing, sample data can be tagged with contextual data, in order to couple identified sample features with various conditions (e.g., perturbations, products, environmental conditions, etc.) in downstream steps of the method. In variations, contextual data can include one or more of: geographic location (e.g., latitude, longitude, altitude); meteorological metadata (e.g., from Dark Sky API); climatic information (e.g., precipitation intensity, precipitation probability, maximum temperature, minimum temperature, dew point, humidity, environmental pressure, wind speed, wind bearing, wind gust, cloud cover, UV index, etc.); environmental disaster information (e.g., fires, hurricanes, tornadoes, earthquakes, temperature variations, etc.); organic management practices (e.g., integrating cultural, biological, and mechanical practices that foster cycling of resources, promote ecological balance, and conserve biodiversity without use of synthetic fertilizers, sewage, irradiation, and genetic engineering); non-organic management practices; use of synthetic fertilizers; use of natural fertilizers; biodynamic management practices (e.g., with generation of their own fertility through composting, integrating animals, cover cropping, and crop rotation); conventional management practices (e.g., with standard farming systems, using a variety of synthetic chemical fertilizers, pesticides, herbicides and other continual inputs, etc.); a regenerative management practices; and/or other practices.

In variations, perturbations associated with the agriculture site(s) and/or crops from which samples are derived can include one or more of: a management practice (e.g., a conventional management practice, an organic management practice, and a biodynamic management practice); a regenerative practice (e.g., application of one or more of a cover crop, silvopasture, managed grazing, intercropping, etc.); a biological input including one or more of: a biostimulant, a biofertilizer, a chemical fertilizer, a soil amendment, a biocontrol agent, a biopesticide, compost, and a biodynamic preparation (wherein the biological input is applied by one or more of: a broadcast spray, an in-furrow spray, seed treatment, application to soil with incorporation, and application to soil without incorporation, etc.); a natural ecological disturbance; and another suitable perturbation.

Data can additionally or alternatively be tagged with metacommunity descriptors, thereby tagging sequence data of the sample dataset with a set of metacommunity descriptors corresponding to a set of communities within a same habitat associated with the agriculture site. In particular, a metacommunity is defined as a group of communities within the same habitat/region/pool associated with each agriculture site associated with the set of samples, where the group(s) of communities display multiple possible arrangements according to environmental filters, dispersal restrictions, priority effects and the latter established interactions. As such, in subsequent steps of the method 100, computing architecture for merging the metacommunity-inferred associations into each of the local communities associated with the set of samples, enables returning of estimations of network properties in all the local communities within the metacommunity, individually, obtaining sample (site)-specific information on microbial ecosystem functioning. Such processes also enable direct comparison among network properties of individual samples, even in the absence of common taxa among them, as all samples are mapped back to the metacommunity, thereby providing a normalization step. Thus, these emergent properties can be implemented as machine-determined universal biomarkers of ecological disturbance.

In relation to model architecture associated with training and refinement of machine learning models described further below, the method described in relation to Block S120 can be used to create training sets of data, in coordination with Block S130 below. As such, training data covering specific sample features and corresponding contextual information related to management practices and other perturbations (e.g., use of various products, environmental perturbations, other agricultural inputs, other practices, etc.) can be used to refine models for predicting effects of various practices and perturbations, and to guide future management practices in a sustainable manner.

In order to process such data, computing platforms implementing one or more portions of the method can be implemented in one or more computing systems, wherein the computing system(s) can be implemented at least in part in the cloud and/or as a machine (e.g., computing machine, server, mobile computing device, etc.) configured to receive a computer-readable medium storing computer-readable instructions. However, Block S120 can be performed using any other suitable system(s).

Sample processing and generating of a sample dataset can be performed according to embodiments, variations, and examples of method steps described in in U.S. application Ser. No. 17/119,972 filed on 11 Dec. 2020, U.S. application Ser. No. 17/587,016 filed on 28 Jan. 2022, and U.S. application Ser. No. 17/665,332 filed on 4 Feb. 2022, incorporated by reference above.

2.2 Methods—Generating Microbiome-Associated Features

Block S130 recites: generating a set of microbiome-associated features for characterization of the set of agricultural samples, upon performing a set of transformation operations upon the sample dataset. Block S130 functions to generate taxonomic annotations, functional annotations, ecological indices, and/or other microbiome-associated features, which can be used for analyses of crops, agricultural site characteristics, and/or other analyses for improving outcomes.

In variations, Block S130 can include generation of taxonomic annotations related to operational taxonomic units (OTUs), amplicon sequence variants (ASVs), diversity metrics (e.g., alpha-diversity metrics, beta-diversity metrics, gamma-diversity metrics, etc.), and/or quantifications of various taxonomic units (e.g., relative quantifications, absolute quantifications).

In variations, Block S130 can include generation of functional annotations related to characterization of nutrient metabolic pathways, species or other organisms that function as plant growth promoters (PGPs, phytohormone producing species, stress tolerance molecule-producing species, etc.), species or other organisms that provide biocontrol functions, organisms that produce disease resistance functions, functional diversity, and/or other suitable functional annotations.

In variations, Block S130 can include generation of ecological indices related to characterization of resilience (e.g., based upon transitivity and modularity of bacterial networks and/or fungal networks), disease risk (e.g., crop-specific disease risks based upon abundances of pathogens and soil microbiome resilience), health (e.g., based upon summary of health and disease risks), sustainable productivity (e.g. trained on known traditional, organic and biodynamic soil samples), combinations of taxonomic indices and functional indices with network properties, and/or other suitable ecological indices.

Categories of microbiome-associated features are described in the following sections.

The invention(s) can additionally or alternatively include aspects described in U.S. application Ser. No. 17/119,972 filed on 11 Dec. 2020, U.S. application Ser. No. 17/587,016 filed on 28 Jan. 2022, and U.S. application Ser. No. 17/665, 332 filed on 4 Feb. 2022, incorporated by reference above.

2.2.1 Taxonomic—Operational Taxonomic Unit (OTU) and Amplicon Sequence Variant (ASV) Processes Variations of Block S130 can include generation of OTU-associated features and/or ASV-associated features for taxonomy annotation.

In relation to OTU-associated features and ASV-associated features, samples can be processed as described in U.S. application Ser. No. 17/119,972 filed on 11 Dec. 2020 (incorporated by reference above) and/or related applications. In particular, processing steps can include sample storage, DNA extraction, amplification (e.g., by a PCR protocol), sequencing (e.g., paired-end sequencing), library preparation (e.g., in relation to 16S rRNA V4 regions, in relation to ITS1 regions, etc.) using custom primers as described above, sequence analysis (e.g., using VSEARCH), and/or other suitable process steps.

In an example, raw paired-end FASTQ sequences (forward and reverse paired reads) were merged, filtered by an expected error 0.25, dereplicated, and sorted by size. Chimera sequences were filtered out in coordination with clustering of non-singleton sequences into 97% identity operational taxonomic units (OTUs) (e.g., a mapping of sequences output by the filtering operation to operational taxonomic units (OTUs) with an identity threshold), or into amplicon sequence variants (ASVs) using a single mismatch (99.7% identity). For OTU-associated features, taxonomic annotation was performed (e.g, using a SINTAX algorithm, using algorithms that implement k-mer similarity metrics to identify top taxonomic candidates for annotation, using algorithms that identify full-length alignments to reference sequences, etc.). In one example, all combined sequences were then mapped to a list of 31,516 OTUs with at least 97% identity, resulting in an OTU table with 54,738,544 sequences, averaging 156,395 sequences per soil sample. The OTU richness of samples averaged 529 OTUs (e.g., in relation to a range of 23-4999 OTUs) per soil sample. OTUs were then classified (e.g., with a UNITE database according to a UTAX pipeline, with a SILVA 123 database through a SILVA-NGS pipeline). However, variations of the example can implement other sequencing protocols, OTU mapping, OTU classification algorithms, and/or other methods.

In variations, the method can additionally or alternatively include processing and assessment of amplicon sequence variants (ASVs). In particular, during sequencing, it is expected that some nucleotide sequences may be subject to sequencing errors; thus, examples of the methods can include clustering of reads to compensate for sequencing errors. In particular, grouping similar sequences to form clusters which are represented by the centroid sequence (i.e., the most abundant sequence of the cluster) can be implemented. In situations where a 97% sequence identity threshold for OTUs is too inclusive for some species, processes of the method can include clusterization between sequences with a difference of only one nucleotide, in order to maintain the highest possible granularity and keep small differences visible, such that they can be annotated separately. Thus, in certain variations, ASV-associated approaches can significantly increase the number of final sequences to annotate for the same sample, increasing resolution and allowing better discrimination of closely related species. The method can thus include performance of annotation of ASVs against curated taxonomic databases based on exact sequence matches, with assessment of in silico performance metrics for the annotation of each ASV. In specific applications, ASVs from 16S regions provided suitable performance metrics (e.g., >90% sensitivity, >90% specificity, >90% positive predictive value, >90% negative predictive value, etc.) for identifying ~46% of the species and ~89% of the genera. ASVs from ITS regions also provided good performance metrics for identifying ~87% of species and ~97% of the genera.

In variations, Bayes factors derived from the posterior odds of a connection between OTUs or ASVs can be used as edge-weights for weighted directed networks, and derivative features processed by models associated with the methods.

2.2.2 Taxonomic—Taxonomic Quantification

In more detail with respect to quantification of sample organisms (e.g., prokaryotes and fungi), variations of Block S130 can include processing a combination of multiple microorganism strains that are added in known amounts to a sample, and running the sample in replication through next generation sequencing (NGS). In examples, two bacterial strains (e.g., a Gram+ and a Gram− strain) can be processed, and each sample can be run in replicate (e.g., one replicate, two replicates, three replicates, four replicates, etc.) for quantification (e.g., absolute quantification of sample microorganisms).

The invention(s) then include extrapolation of a number of 16S copies from the microorganism strains added in known concentrations in relation to the rest of the microorganisms in the sample, and then correcting by 16S copy number to obtain the final absolute concentration of each organism (e.g., bacterial organism, archaeal organism) present.

In variations, the invention(s) can additionally or alternatively implement a synthetic construct having an example format:

[16S FW Primer][its FW Primer][Random Seq Based on 16S and ITS][16S RV Complement Primer][its RV Complement Primer].

In examples, the [RANDOM SEQ BASED ON 16S AND ITS] can have desired aspects. In one such example, the random sequence is composed of a portion (e.g., first half) of a 16S amplicon from a first organism (e.g., *Rhizobium pusense*) and a portion (e.g., first half) of an ITS amplicon from a second organism (e.g., *Solicoccozyma phenolica*), after which the nucleotide order was shuffled randomly. In this example, the [RANDOM SEQ BASED ON 16S AND ITS] has the desired sequence; however, in other examples, the random sequence can be generated in another suitable manner (e.g., based upon shuffling of sequence portions from other amplicons of other organisms).

In the example above, the random sequence has a 46% GC and is not similar to any sequence in the NT database, so is unique enough to be distinguished from extant bacteria and fungi. The invention(s) also include steps for evaluating and detecting potential secondary structures of the synthetic construct to ensure it is in a similar energy range to that of an ITS amplicon, or that of a 16S amplicon. However, the random sequence can have another suitable format.

In relation to quantification, Block S130 can include addition of synthetic spike to samples in known concentration, in order to perform absolute quantification of sample organisms (e.g., prokaryotes and fungi) simultaneously. In variations, the synthetic spike (e.g., of exogenous bacteria with known microbial composition into samples) can be run in replication (e.g., one sample with no replication, two replicates, three replicates, etc,). Furthermore, in other variations, the synthetic spike can be used to quantify several sample types (e.g., soils, soil amendments, tissue samples, produce samples, etc.).

Taxonomic annotation data in relation to quantification can be presented at any taxonomic level (i.e. phylum, class, order, family, genus, species, subspecies).

Additionally or alternatively, taxonomic annotation can be presented in relation to ratios between different types of organisms (e.g., a bacterial:fungal ratio, an endomycorrhizae:ectomycorrhizae ratio, or any other suitable ratio).

In examples, shown in FIGS. 2A-2F, taxonomic features can include descriptions of detected populations (e.g. microbial population distributions, fungal population distributions), with breakdowns of compositions (e.g., in percentages) for different taxonomic groups/ranks. Exemplary representative bacterial phylum distributions (e.g., Firmicutes, proteobacteria, bacteroidetes, planctomycetes, actinobacteria, etc.) and representative fungal phylum distributions (e.g., ascomycota, basidiomycota, zygomycota, glomeromycota, etc.) are depicted in FIGS. 2A-2F, with additional features associated with quantification of specific species (e.g., *Bacillus* licheniformis, *Clostridium* isotidis, *Bacillus subtilis, Escherichia coli, Bacillus amyloliquefaciens, Bacillus megaterium*, etc.). However, variations of the example features can be returned by outputs of Block S130.

2.2.3 Taxonomic—Diversity Metrics

In more detail with respect to generation of diversity features with respect to taxonomic annotation, variations of Block S130 can include steps for performing alpha-, beta-, and/or gamma-diversity analyses in relation to various taxonomic groups and/or associated features. For instance, variations of the method include steps for performing alpha- and beta diversity analyses using 16S and ITS ASV or OTU counts (e.g., using R vegan), where alpha-diversity metrics (e.g., Shannon, richness, etc.) were calculated and plotted across all covariates available. In relation to various inputs and/or practices, Block S130 can implement architecture for performing tests (e.g., Wilcoxon rank-sum tests) to compare samples associated with different inputs and/or management practices (e.g., control and treatment groups) within various subgroups.

In variations of Block 130, alpha-diversity analyses can include rarefaction of samples to a common desired sequencing depth (e.g., 20,000 reads, 10,000 reads, etc.) and replicating the rarefaction a number of times to ensure the results of the subsample are representative of the entire sample (e.g., repeating 10 times, repeating 50 times, repeating 100 times, repeating 500 times, etc.)

For beta-diversity, the Block S130 can implement architecture for determining beta-diversity characteristics. For instance, in one variation, Block S130 includes steps for implementing Kruskal's non-metric multidimensional scaling in conjunction with Aitchison distances. Block S130 can also implement architecture for performing permutational multivariate analysis of variance on the Aitchison distance matrix, using all possible combinations of the location, timepoint and treatment variables.

However, other variations of methods for characterizing diversity metrics and/or other statistical methods can be implemented.

2.2.4 Taxonomic—Abundance

Block S130 can also implement architecture for determining abundance parameters (e.g., relative abundances) in relation to various groups of organisms, for various analyses. For instance, in one such variation, relative/absolute abundance parameters determined from outputs of Block S130 can be used for determination of crop-specific disease risk or other insights, in relation to variations of method steps described in more detail below.

In some variations, Block S130 can thus apply sample processing techniques and data processing steps associated with determining relative and absolute abundance of various groups (e.g., groups of kingdoms, phyla, classes, orders, families, genera, species, subspecies, strains, infraspecies taxa, etc.) represented in samples from the agricultural site(s), with direct measurements and/or functional inference based on the taxonomic abundances and/or ecological network factors.

In a specific example related to abundance-associated features, Block S130 can include implementation of methods for determining differential abundance of various OTUs/ASVs. In more detail, in a specific example, zero counts in data were replaced, where valid values for replacement were calculated under a Bayesian paradigm, assuming a Dirichlet prior. Non-zero values were then adjusted to maintain the overall composition using a pairwise comparison process for differential expression analysis (e.g., edgeR algorithm), thereby determining differential abundance of various groups represented in a sample.

Outputs of Block S130 can then be used for responding to an issue detected at the agriculture site(s) being assessed (e.g., in relation to pathogen presence or increased abundance of a detrimental microorganism, in relation to decreased abundance of a beneficial microorganism, in relation to correcting a perturbation, in relation to adjusting application of a product at the agriculture site, implementing protective measures against environmental effects, etc.); responding to or otherwise correcting other undesired statuses at one or more agriculture sites being monitored; providing information regarding site characteristics to a manager/operator/other entity associated with the agriculture site(s); performing decision-making guidance (e.g., in relation to analyses indicative of sustainability of practices, in relation to long term effects of use of one or more products, etc.); and performing other suitable actions, described in more detail below.

The method can, however, include other method steps and/or process outputs based upon abundance measurements in another suitable manner.

In examples, relative abundance features can include relative abundances of taxonomic groups (e.g., genus and species, other taxonomic groups), where exemplary fungal groups shown include: *Trichoderma* atroviride, *Wallemia mellicola*, *Penicillium dierckxii*, *Naganishia diffluens*, *Penicillium rubens*, *Alternaria alternata*, *Epicoccum nigrum*, *Talaromyces marneffei*, *Penicillium citrinum*, *Coniothyrium* sp. *Xenomyrothecium tongaense*, *Resinicium rimulosum*, *Meyerozyma guilliermondii*, *Candida tropicalis*, *Wallemia hederae*, *Chaetomium globosum*, *Aspergillus fumigatus*, *Ganoderma applanatum*, *Coprinopsis gonophylla*, *Aspergillus terreus*, *Wallemia sebi*, *Cladosporium herbarum*, *Alternaria metachromatica*, *Fusarium oxysporum*, *Nigrospora oryzae*, *Arachnomyces pilosus*, *Penicillium pimiteouiense*, *Wallemia* sp., *Aspergillus pseudoglaucus*, *Ovatospora medusarum*, *Lophotrichus fimeti*, *Rhizophagus irregularis*, *Neofavolus alveolaris*, *Penicillium melinii*, *Penicillium herquei*, *Trichosporon asahii*, *Aspergillus versicolor*, *Penicillium erubescens*, *Humicola olivacea*, *Penicillium cinnamopurpureum*, *Schizothecium inoequale*, *Rhizopus oryzae*, *Penicillium parvulum*, *Penicillium brevicompactum*, *Penicillium restrictum*, *Zopfiella erostrata*, *Collariella bostrychodes*, *Aspergillus* sp, *mycosphaerella coffeicola*, *Penicillium polonium*, etc. However, variations of the example features can be returned by outputs of Block S130.

Furthermore, outputs of Block S130 can further implement steps for functional annotation and/or generation of ecological indices as described in related applications and below, which can be processed individually and/or in combination with taxonomic annotation in relation to generation of agronomic indices based upon one or more of taxonomic annotations, functional annotations, and ecological indices.

Figure 1C:
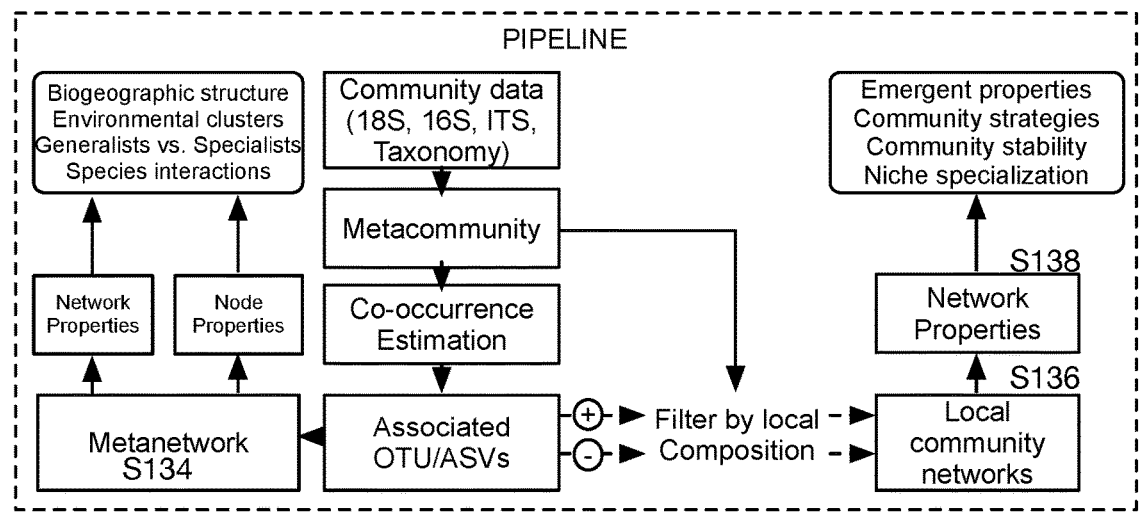
FIG. 1C depicts a schematic of a workflow and framework of a methodology for assessing agriculture practices and inputs, with respect to generating network properties.
Figure 1C:
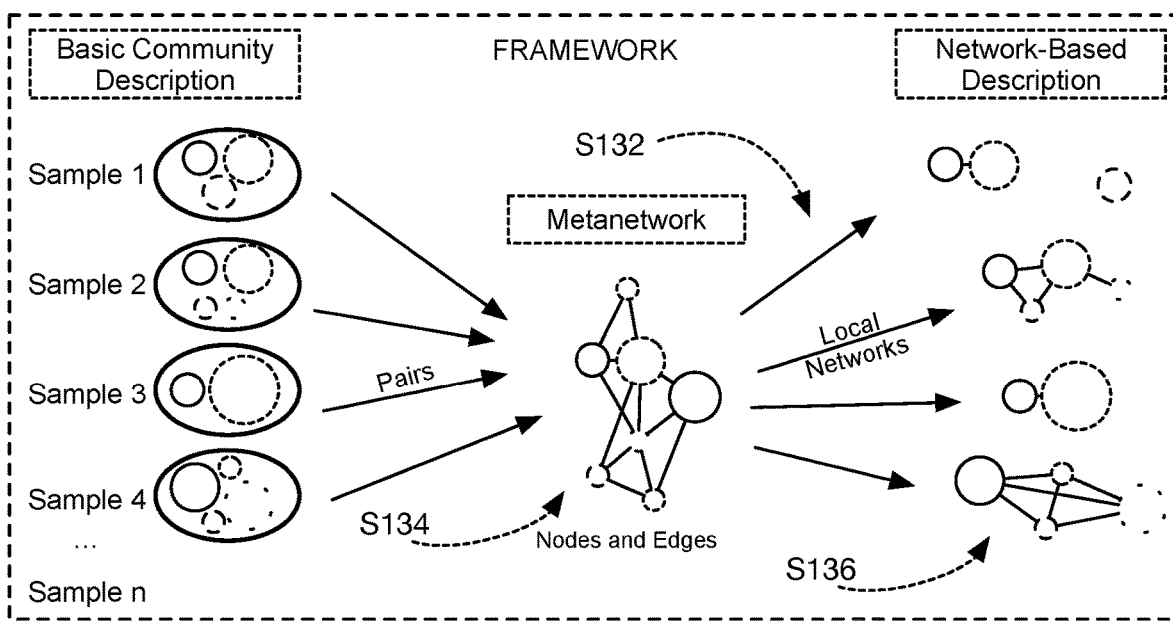
Figure 1D:
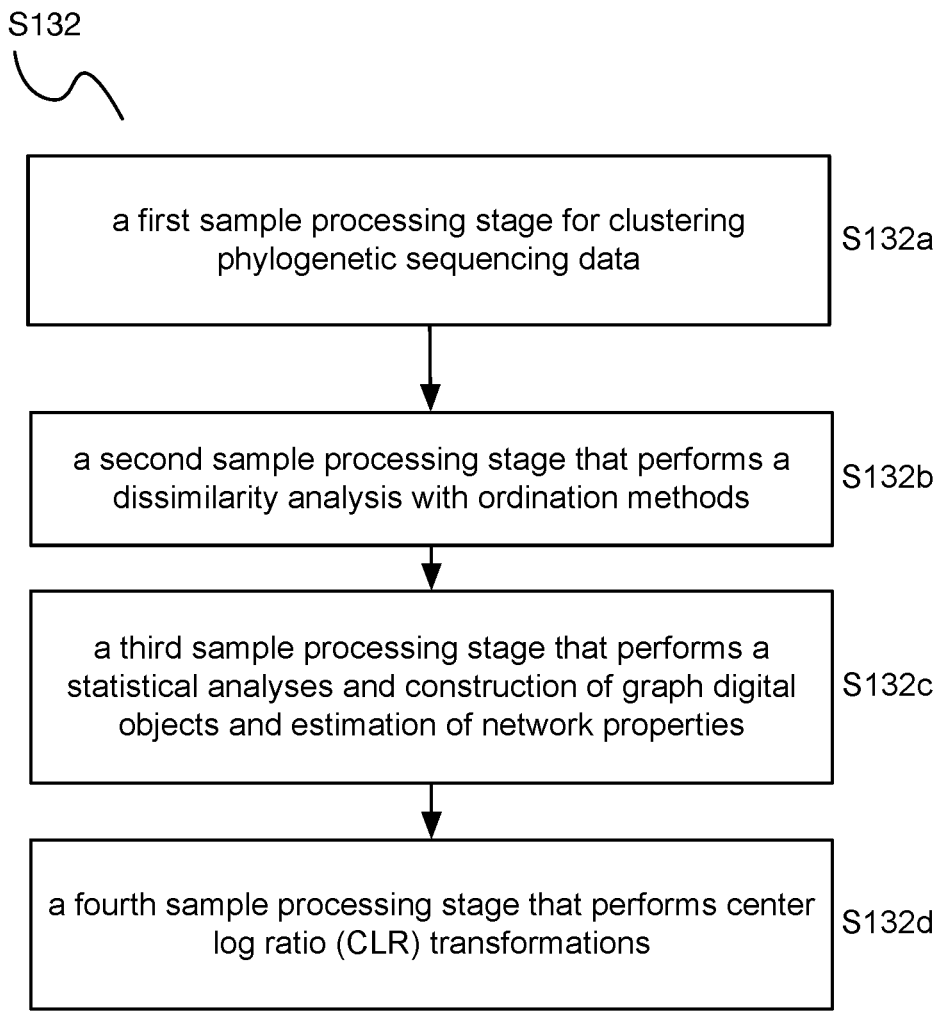
FIG. 1D depicts a portion of a methodology for assessing agriculture practices and inputs, with respect to generating network properties.
Figure 1E:
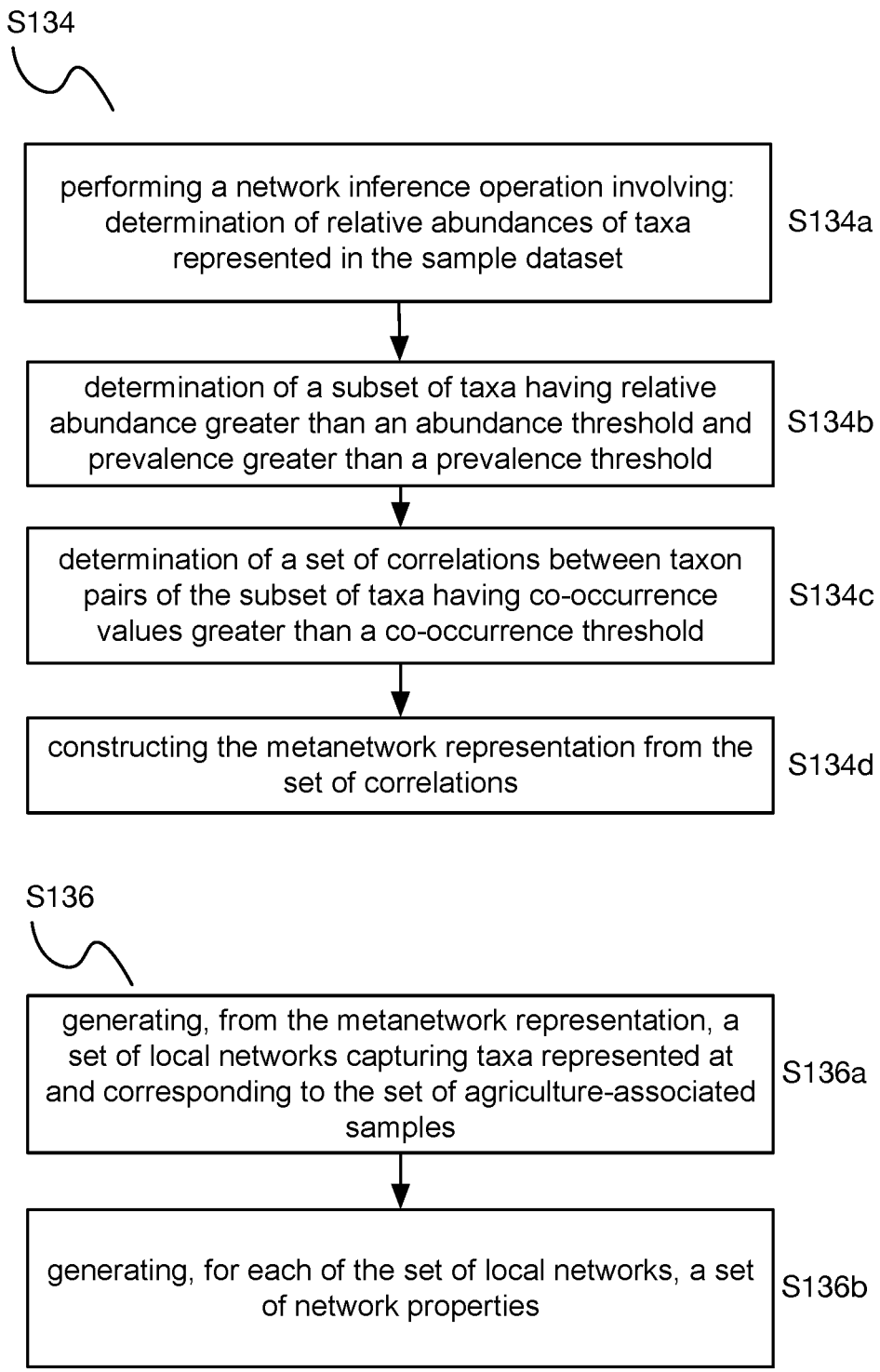
FIG. 1E depicts a portion of a methodology for assessing agriculture practices and inputs, with respect to generating network properties.

2.2.4.1 Improvements in Network Inference Based Upon Metanetwork and Local Network Construction As shown in FIGS. 1C, 1D, and 1E, Block S130 can include construction of metanetwork and local networks S132 associated with and/or from which additional features of the set microbiome-associated features can be extracted. In particular, in relation to existing approaches (e.g., based on methods for detection of presence/absence of network components), embodiments, variations, and examples of step S132 described efficiently return quantitative outputs indicative of correlation strength, which can be used to generate shortest-path calculations and support downstream portions of the method. In variations, improvements include implementation of object transformation functions to reduce compositionality-associated errors, include implementation of architecture for combination of 16S-associated elements and ITS-associated elements from the sample dataset of Step S120 in order to carry out inter-kingdom network inferences in a novel manner (e.g., constructing metanetwork representations and/or local networks with a combination of 16S and ITS components), which further provides improvements in performance of systems for generating characterizations with rapid outputs and reduce error in model results. Variations of system architecture further replacement crop-based references with cluster references. In particular, some models implement assignment of crop references for less common crops, and cluster references can instead be applied in a manner that does not require expert input/evaluation of suitability of a particular crop reference for a less common crop.

In particular, examples of the methods for construction of metanetworks and local networks (e.g., implementing Spearman-based approaches) described can produce an 100-fold decrease in detected associations when using source data, and additional examples implementing optimized source data (e.g., to increase power) can produce a median 34-fold decrease in detected associations. Due to the error-reducing strategies implemented, a majority of this decrease is likely due to errors. Variations of the methods described can produce a 10-fold, 20-fold, 30-fold, 40-fold, 50-fold, 60-fold, 70-fold, 80-fold, 90-fold, 100-fold, 150-fold, 200-fold, any intermediate value, or greater than 200-fold decrease in detected associations, thereby drastically improving performance of the technology in relation to generation of outputs.

In variations (as shown in FIG. 1D), the sample dataset can be generated upon: implementing a first sample processing stage S132a for clustering phylogenetic sequencing data (e.g., into OTUs, into ASVs, etc.), followed by implementing a second sample processing stage S132b that performs a dissimilarity analysis with ordination methods. Step S132 can further implement a third sample processing stage that performs a statistical analyses and construction of graph digital objects and estimation of network properties S132c, followed by performance of a fourth sample processing stage that performs center log ratio (CLR) transformations S132d upon outputs of Step S132c using analyses for: amounts, or open compositions, in a real, classical geometry, amounts in a logarithmic geometry, closed compositions in a real geometry, or closed compositions in a logistic geometry, following a log-ratio approach. Further data processing architecture can be implemented, in relation to processing large amounts of data in a manner that cannot be implemented practically by the human mind.

Clustering of phylogenetic sequencing data in Step S132a can be performed for genomic, transcriptomic, and/or protein data, with one or more of: single-linkage clustering, greedy clustering with identification of representative sequences of clusters, and iterative reassignment of sequences to clusters based upon similarity calculations, and/or other techniques. Clustering algorithms can be based upon one or more of: K-means, CD-HIT, UCLUST in USEARCH, Starcode, OrthoFinder Linclust, TribeMCL, BAG, JESAM, UICluster, BLASTClust single-linkage clustering, Clusterer, PATDB, nrdb, CluSTr, ICAtools, Skipredudant EMBOSS, CLUSS, CLUSS2 Algorithm, and/or other suitable algorithms.

Dissimilarity analyses of Step S132b can be performed with one or more of, a combination of, a derivative of, or an adjustment to one or more of: a Gower index generation technique, Bray-Curtis index generation technique, a Jaccard and Kulczynski index generation technique (e.g., for detection of underlying ecological gradients; a Morisita index generation technique, a Horn-Morisita index generation technique, a Binomial index generation technique, a Cao and Chao index generation technique (e.g., for processing different sample sizes; a Mountford index generation technique, a Raup-Crick index generation technique for presence-absence data (e.g., for handling unknown and variable sample sizes). However, dissimilarity analyses can be otherwise performed.

Performance of center log ratio (CLR) transformations S132d upon outputs of Step S132c can improve compositionality characterizations (e.g., in relation to traditional Spearman approaches), with characterizations of combinations of 16S-associated elements and ITS-associated elements for carry out of inter-kingdom network inferences.

In relation to Step S132 and substeps, traditional methods of clustering involve use of one or more reference sets of representative samples of similar crops to perform clustering. Use of reference crops, however, traditionally requires expert knowledge for analyses of crops having insufficient samples. The methods described here, in contrast, can provide improved performance with architecture for automatic assignment of samples to reference sets without use of representative crops and assignment by an expert.

In a specific example, clustering of data in Step S132a involves implementation of genus-level (or other taxonomic-level) relative abundances to perform a principal coordinate analysis (PCoA) using dissimilarity measurements (e.g., Bray-Curtis dissimilarity). K-means clustering (e.g., with a K factor of 15) was then used to separate samples into clusters based upon the dissimilarity measurements, and cluster number was selected based on evenness of cluster size following cluster assignment. Representative samples were sampled randomly according to the frequency of representative crop types in a cluster. Variations of the specific example can implement other dissimilarity indices (some of which are described above), with other clustering algorithms (described) above, and/or other K factor values (e.g., 3, 4, 5, 6, 7, 8, 9, 10, 11, 12, 13, 14, 16, 17, 18, 19, 20, greater than 20, etc.) for variations involving K-means clustering.

The randomly-sampled representative samples were then used to construct the metanetwork for the specific example described in relation to Step S134 below, where dissimilarity indices were calculated between each respective sample and a subset of samples (e.g., 2 samples, 3 samples, 4 samples, 5 samples, greater than 5 samples, etc.) closest to centroids of clusters generated in Step S132a. All representative samples for the cluster with lowest dissimilarity were included for metanetwork inference in Step S134.

As such, outputs of Step S132 were processed to construct metanetwork representations of the one or more agriculture sites S134, followed by generating, from the metanetwork representation, a local network capturing taxa represented at and corresponding agriculture-associated sample S136. The method can then generate, for each local network, a set of network properties S138 which can be processed in the analysis of step S140. In relation to utility, metanetworks using large spatial scales have can thus be applied to provide insights into the organization and environmental preferences of microbiome organisms, types of interactions, generalist versus specialist strategies of particular microbiome organisms, or even ecological guilds according to potential biotic interactions once the effect of the environment has been removed, thereby providing global characterizations of particular metacommunities. Then, from the metanetworks, local networks can be extracted to provide insights into the actual arrangements of taxa in local communities, where taxa may be loosely or densely connected or display local adaptations to niches or functional guilds. Inferring the local network properties of individual samples characterizes the microbiome of a given sample in terms of its association structure, providing a unique layer of information when studying the biodiversity and stability at the abstraction level of a specific sample or monitoring its evolution in time and during environmental disturbances, where analysis of the sample in isolation does not provide the same level of information as analysis of the sample in the context of the metanetwork community.

As shown in FIG. 1E, construction of the metanetwork representation in Step S134 can include, performing a network inference operation involving: determination of relative abundances of taxa represented in the sample dataset S134a, determination of a subset of taxa having relative abundance greater than an abundance threshold and prevalence greater than a prevalence threshold S134b, determination of a set of correlations between taxon pairs of the subset of taxa having co-occurrence values greater than a co-occurrence threshold S134c, and constructing the metanetwork representation from the set of correlations S134d.

In relation to Step S134a, determination of relative abundances of taxa represented in the sample dataset can include determination of genus-level and/or other taxonomic level relative abundances, embodiments, variations, and examples of which are described in Section 2.2.4 above. Relative abundances processed with center-log-ratio transformations described above were used for metanetwork inference; however, other derivatives or transformations of abundances (e.g., relative abundances, absolute abundances, etc.) can be used.

In relation to Step S134b, determination of a subset of taxa having relative abundance greater than an abundance threshold and prevalence greater than a prevalence threshold, can include implement suitable thresholds. In a specific example, only taxonomic groups (e.g., genera, species, etc.)

having prevalence over 10% were included for further analysis, and correlations (e.g., Spearman correlations) between taxon pairs were inferred with a non-zero abundance threshold for pairs having at least 10 co-occurrences, where methods for determining co-occurrence and co-exclusion factors are described herein. While a prevalence threshold of 10% is described, alternative variations can implement a prevalence threshold of greater than 5%, 6%, 7%, 8%, 9%, 15%, 20%, or another suitable threshold. Furthermore, while an abundance threshold of non-zero is described, alternative variations can implement an abundance threshold that is different than non-zero.

In relation to Step S134c, determination of a set of correlations between taxon pairs of the subset of taxa having co-occurrence values greater than a co-occurrence threshold can include determination of correlations (e.g., Spearman correlations) between taxon pairs satisfying a non-zero abundance threshold for pairs having at least 10 co-occurrences, where methods for determining co-occurrence and co-exclusion factors are described herein. While a co-occurrence threshold of 10 is described, the co-occurrence threshold can be at least 5, 6, 7, 8, 9, 15, 20, or another suitable number. Alternatively, a co-exclusion factor can be implemented for generating correlations between taxon pairs. As such, Steps S134b-134c can be performed in a manner that avoids inference of spurious correlations introduced by false zeros. In examples, p-values of the correlations were corrected for multiple comparisons with a correction operation (e.g., the Benjamini-Hochberg correction), and only correlations with a p-value below 0.05 were retained; however, other correlation strength estimates can be used to reduce false positives in returned outputs (e.g., in order to reduce the number of false zeroes returned).

Following construction of metanetworks in Step S134, a set of local networks capturing taxa represented at and corresponding to the set of agriculture-associated samples can be constructed in Step S136. Step S136 can include: generating, from the metanetwork representation, a local network capturing taxa represented at and corresponding to each of the set of agriculture-associated samples S136a, and generating, for each respective local network, a set of network properties S136b.

In more detail with respect to step S136a, a subgraph was extracted for each sample in order to generate a local network containing only taxa detected in that specific sample. As such, each local network corresponds to and captures taxa of the metanetwork specific to each respective sample.

In relation to Step S136b, in examples, the set of network properties can include properties derived from co-exclusion networks and co-occurrence networks, such as transitivity, assortativity, and/or other properties/parameters described in applications incorporated by reference. Network properties can be determined for different types of organism communities (e.g., bacterial communities, fungal communities, etc.) independently of each other or in an aggregated manner. In variations, network properties can include one or more of (e.g., in relation to networks with nodes and edges): connected components (e.g., a subnetwork in which any two nodes connect to each other by edges, that lack connection to any other node in the full network); clustering coefficient (e.g., the measure of the degree to which nodes in a graph tend to cluster together in terms of connected triangles (three nodes that are connected with three edges) in the network); average path length (e.g., mean of the minimal number of required edges to connect any two nodes); modularity (e.g., the measure of the strength of a partition into modules (groups of nodes)); partitioning factor (e.g., proportion of edges inside modules compared to the proportion of edges between them); average path length between nodes of a network (where correlation strength can be used to process average path length calculations to further reduce false positive number); a similarity property characterizing similarity of local networks to metanetworks; an assortativity measure characterizing similarity of nodes to neighboring nodes; a centrality property describing connectedness of nodes; a centralization property describing ratios between observed centrality and theoretical maximum centrality; an eigenvalue property describing a largest eigenvalue of a matrix representation of at least one local network; an articulation property describing a number of nodes that would fragment at least one local network upon deletion; a clique property that describes a number of cliques which cannot be generalized to larger cliques, wherein a clique is a group of nodes connected to all other nodes in the clique; co-exclusion associated factors, co-occurrence associated factors, and/or other factors, embodiments, variations, and examples of which are also covered in applications incorporated by reference. In specific examples, network properties can further include combinations of or derivatives of network properties (e.g., inverse relationships between clustering coefficient and average path length as an indication of how densely connected networks are).

With respect to modularity, modularity can indicate the degree of separation of the network into modular components and separate groups of organisms below the level of community that have a shared mix of associations. This shared mix of associations may be present for multiple reasons. Since associations across the spatial scale mostly reflect the presence of thresholds or constraints provided by the environment, inputs, and practices, presence of modules at large spatial scales can be attributed to these factors. Furthermore, modularity can be attributed to one or more of: (i) multiple sets of OTUs/ASVs that may change depending on the environmental situation in a community; (ii) sets of OTUs/ASVs that reflect microscale niches present in topsoil versus deeper soil; (iii) independent environmental factors (e.g., pH level, temperature, input, practice, etc.); (iv) functional guilds, with each guild with independent affinities. Modularity and positive and negative relationships between network properties can thus provide insights into niche specialization vs. collective aggregation, and high vs. low competitive exclusion. Tracking such network properties, in relation to Steps S140 and S150 of the method, can thus be used to evaluate inputs and practices and to generate instructions for execution of actions at various agriculture sites, in relation to Step S160.

In a specific example, Step S136 included identification of network clusters using the fast greedy modularization algorithm. Furthermore, in order to adapt methods for evaluating the correlation-based microbiome networks, Step S136 implemented architecture for generating a variant of weighted assortativity, where the architecture included structures for processing ratios of positive and negative correlations in a node's neighborhood, rescaling the correlations to an integer (e.g., an integer between 1 and 4) and using the rescaled value to calculate assortativity. For properties that cannot take negative values (e.g., in relation to the diameter, average weighted path length and the clustering algorithm), correlations were rescaled to a range (e.g., 0,1). Finally, the node and edge Jaccard similarity of the local networks to the metanetworks was calculated as a validation step.

However, variations of generating network properties from metanetwork constructions and local network constructions can be otherwise performed.

2.2.5 Functional—Nutrient Metabolic Pathways

In more detail with respect to generation of features related to nutrient metabolic pathways, Block S130 can include steps for predicting metagenomic composition of a sample based on sequences (e.g., amplicon sequences, sequences associated with operational taxonomic units, etc.) processed according to embodiments, variations, and examples of Block S120 above. In variations, however, full metagenomic sequences can be obtained for the samples, at appropriate sequencing depth, so enzyme sequences can be directly annotated from raw sequencing data as opposed to being predicted based on amplicon sequencing. Data associated with metagenomic composition can then be processed further and transformed to extract features related to nutrient metabolic pathways, with respect to effects of sample microbiota upon soil macronutrients and micronutrients.

In one variation, Block S130 can include generating predicted metagenomic functional factors/composition of one or more samples acquired from the agricultural site(s), wherein generating the predicted metagenomic composition comprises extracting functional annotations associated with the sequences from a suitable database (e.g., a custom database, the Kyoto Encyclopedia of Genes and Genomes (KEGG) database, etc.). Block S130 can then include architecture for identifying specific enzymes from the metagenomes, in relation to those specific enzymes most informative for each type of nutrient metabolic cycle in soil. As such, outputs of Block S130 can include features associated with enzymes corresponding to each nutrient metabolic pathway, with scores at pathway-level (e.g., aggregate) and nutrient-level scales.

In examples, outputs of Block S130 can include features associated with carbon pathways (e.g., carbon fixation, aerobic respiration, fermentation, methanogenesis, organic matter release, in terms of percentages, in terms of gain and loss, in terms of supply, in terms of competition, in terms of indirect benefits, etc.) with respect to specific enzyme annotations derived from suitable databases. In examples, enzymes associated with carbon pathways can include one or more of: ribulose-bisphosphate carboxylase large or small chain [EC:4.1.1.39], cytochrome c oxidase subunit I [EC:1.9.3.1], 2-oxoglutarate/2-oxoacid ferredoxin oxidoreductase subunit alpha [EC:1.2.7.3 1.2.7.11], fumarate reductase flavoprotein subunit [EC:1.3.5.4], methane monooxygenase component A alpha or beta chain [EC:1.14.13.25], aerobic carbon-monoxide dehydrogenase small or large subunit [EC:1.2.5.3], L-lactate dehydrogenase [EC:1.1.1.27], methyl coenzyme M reductase system, component A2, methyl-coenzyme M reductase beta subunit [EC:2.8.4.1], acetyl-CoA decarbonylase/synthase complex subunit [EC:2.1.1.245], endoglucanase [EC:3.2.1.4], endo-1,3(4)-beta-glucanase [EC:3.2.1.6], beta-glucuronidase [EC:3.2.1.31], cellulose 1,4-beta-cellobiosidase [EC:3.2.1.91], beta-glucosidase [EC:3.2.1.21], cellobiose epimerase [EC:5.1.3.11], chitinase [EC:3.2.1.14], chitin deacetylase [EC:3.5.1.41], putative chitinase, chitin-binding protein, bifunctional chitinase/lysozyme [EC:3.2.1.14 3.2.1.17], endo-1,4-beta-xylanase [EC:3.2.1.8], xylan 1,4-beta-xylosidase [EC:3.2.1.37], mannan endo-1,4-beta-mannosidase [EC:3.2.1.78], arabinogalactan endo-1,4-beta-galactosidase [EC:3.2.1.89], galactonate dehydratase [EC:4.2.1.6], alpha-D-xyloside xylohydrolase [EC:3.2.1.177], oligosaccharide reducing-end xylanase [EC:3.2.1.156], arabinoxylan arabinofuranohydrolase [EC:3.2.1.55], glucuronoarabinoxylan endo-1,4-beta-xylanase [EC:3.2.1.136], catechol 2,3-dioxygenase [EC:1.13.11.2], biphenyl 2,3-dioxygenase subunit alpha [EC:1.14.12.18], naphthalene 1,2-dioxygenase subunits [EC:1.14.12.12 1.14.12.23 1.14.12.24], cis-1,2-dihydro-1,2-dihydroxynaphthalene/dibenzothiophene dihydrodiol dehydrogenase [EC:1.3.1.29 1.3.1.60], biphenyl 2,3-dioxygenase subunit beta [EC:1.14.12.18], or other suitable enzymes.

In examples, outputs of Block S130 can include features associated with nitrogen pathways (e.g., inorganic nitrogen cycle health, inorganic nitrogen consumption, inorganic nitrogen release, in terms of percentages, in terms of gain and loss, in terms of supply, in terms of competition, in terms of indirect benefits, etc.) with respect to specific enzyme annotations derived from suitable databases. In examples, enzymes associated with nitrogen pathways can include one or more of: nitrite reductase (cytochrome c-552) [EC:1.7.2.2], hydroxylamine dehydrogenase [EC:1.7.2.6], nitrite reductase (NO-forming) [EC:1.7.2.1], nitrous-oxide reductase [EC:1.7.2.4], nitric oxide reductase subunit C, nitric oxide reductase subunit B [EC:1.7.2.5], nitrite reductase (NO-forming)/hydroxylamine reductase [EC:1.7.2.1 1.7.99.1], glutamate synthase (NADPH/NADH) large chain [EC:1.4.1.13 1.4.1.14], glutamate synthase (ferredoxin) [EC:1.4.7.1], assimilatory nitrate reductase electron transfer subunit [EC:1.7.99.–], ferredoxin-nitrate reductase [EC:1.7.7.2], nitrogenase delta subunit [EC:1.18.6.1], glutamine synthetase [EC:6.3.1.2], nitrogenase molybdenum-iron protein alpha chain [EC:1.18.6.1], nitrogenase iron protein NifH [EC:1.18.6.1], nitrogenase molybdenum-iron protein beta chain [EC:1.18.6.1], glutamate dehydrogenase [EC:1.4.1.2], glutamate dehydrogenase (NAD(P)+) [EC:1.4.1.3], periplasmic nitrate reductase NapA [EC:1.7.99.–], cytochrome c-type protein NapB, nitrate reductase/nitrite oxidoreductase, alpha subunit [EC:1.7.5.1 1.7.99.–], nitrate reductase/nitrite oxidoreductase, beta subunit [EC:1.7.5.1 1.7.99.–], methane/ammonia monooxygenase subunits [EC:1.14.18.3 1.14.99.39], or other suitable enzymes.

In examples, outputs of Block S130 can include features associated with phosphorus pathways (e.g., inorganic phosphorus assimilation, organic phosphorus assimilation, phosphorus solubilization, phosphorus consumption in terms of percentages, in terms of gain and loss, in terms of supply, in terms of competition, in terms of indirect benefits, etc.) with respect to specific enzyme annotations derived from suitable databases. In examples, enzymes associated with phosphorus pathways can include one or more of: phosphate transport system ATP-binding protein [EC:3.6.3.27], phosphate transport system permease protein, low-affinity inorganic phosphate transporter, GntR family transcriptional regulator, phosphonate transport system regulatory protein, 2-aminoethylphosphonate-pyruvate transaminase [EC:2.6.1.37], phosphonoacetaldehyde hydrolase [EC:3.11.1.1], ribose 1,5-bisphosphokinase [EC:2.7.4.23], alpha-D-ribose 1-methylphosphonate 5-triphosphate synthase subunit PhnL [EC:2.7.8.37], putative phosphonate transport system ATP-binding protein, alpha-D-ribose 1-methylphosphonate 5-triphosphate diphosphatase [EC:3.6.1.63], alpha-D-ribose 1-methylphosphonate 5-phosphate C—P lyase [EC:4.7.1.1], alpha-D-ribose 1-methylphosphonate 5-triphosphate synthase subunits [EC:2.7.8.37], phosphonate transport system ATP-binding protein [EC:3.6.3.28], phosphonate transport system permease protein, phosphonate transport system substrate-binding protein, PhnB protein, protein PhnA, pyrroloquinoline-quinone synthase [EC:1.3.3.11], or other suitable enzymes.

In examples, outputs of Block S130 can include features associated with potassium pathways (e.g., potassium consumption, potassium solubilization, in terms of percentages, in terms of gain and loss, in terms of supply, in terms of competition, in terms of indirect benefits, etc.) with respect to specific enzyme annotations derived from suitable databases. In examples, enzymes associated with potassium pathways can include one or more of: trk system potassium uptake protein, two-component system, OmpR family, sensor histidine kinase KdpD [EC:2.7.13.3], two-component system, OmpR family, KDP operon response regulator KdpE, KUP system potassium uptake protein, pyrroloquinoline-quinone synthase [EC:1.3.3.11], or other suitable enzymes.

In examples, outputs of Block S130 can include features associated with iron pathways (e.g., iron assimilation, etc.) with respect to specific enzyme annotations derived from suitable databases. In examples, enzymes associated with iron pathways can include one or more of: enterobactin synthetase component D [EC:6.3.2.14 2.7.8.–], enterobactin synthetase component F [EC:6.3.2.14], MFS transporter, ENTS family, enterobactin (siderophore) exporter, ATP-binding cassette, subfamily B, salmochelin/enterobactin exporter, ferric enterobactin receptor, outer membrane receptor for ferrienterochelin and colicins, ferrous iron transport proteins, or other suitable enzymes.

In examples, outputs of Block S130 can include features associated with zinc pathways (e.g., zinc transport equilibrium, etc.) with respect to specific enzyme annotations derived from suitable databases. In examples, enzymes associated with zinc pathways can include one or more of: cobalt-zinc-cadmium efflux system protein, zinc transport system substrate-binding protein, zinc transport system permease protein, zinc transport system ATP-binding protein [EC:3.6.3.–], or other suitable enzymes In examples, outputs of Block S130 can include features associated with manganese pathways (e.g., manganese transport equilibrium, in terms of percentages, in terms of gain and loss, in terms of supply, in terms of competition, in terms of indirect benefits, etc.) with respect to specific enzyme annotations derived from suitable databases. In examples, enzymes associated with phosphorus pathways can include one or more of: manganese/zinc transport system substrate-binding protein, manganese/zinc transport system permease protein, manganese/zinc transport system ATP-binding protein [EC:3.6.3.35], manganese transport protein, manganese transport system substrate-binding protein, or other suitable enzymes.

In examples, outputs of Block S130 can include features associated with sulfur pathways (e.g., sulfur cycle equilibrium, in terms of percentages, in terms of gain and loss, in terms of supply, in terms of competition, in terms of indirect benefits, etc.) with respect to specific enzyme annotations derived from suitable databases. In examples, enzymes associated with sulfur pathways can include one or more of: adenylylsulfate kinase [EC:2.7.1.25], sulfate adenylyltransferase subunit 1 [EC:2.7.7.4], sulfate adenylyltransferase subunit 2 [EC:2.7.7.4], thiosulfate reductase/polysulfide reductase chain A [EC:1.8.5.5], cysteine dioxygenase [EC:1.13.11.20], thiosulfate/3-mercaptopyruvate sulfurtransferase [EC:2.8.1.1 2.8.1.2], adenylylsulfate reductase, subunits [EC:1.8.99.2], dissimilatory sulfite reductase alpha subunit [EC:1.8.99.5], sulfur-oxidizing proteins, or other suitable enzymes.

In examples, outputs of Block S130 can include features associated with calcium pathways (e.g., calcium transport, etc.) with respect to specific enzyme annotations derived from suitable databases. In examples, enzymes associated with calcium pathways can include one or more of: Ca2+:H+ antiporter, cation:H+ antiporter, or other suitable enzymes.

In examples, outputs of Block S130 can include features associated with copper pathways (e.g., copper export, in terms of percentages, in terms of gain and loss, in terms of supply, in terms of competition, in terms of indirect benefits, etc.) with respect to specific enzyme annotations derived from suitable databases. In examples, enzymes associated with copper pathways can include one or more of: Cu+-exporting ATPase [EC:3.6.3.54], outer membrane protein, Cu(I)/Ag(I) efflux system, or other suitable enzymes.

In examples, outputs of Block S130 can include features associated with chlorine pathways (e.g., chlorine transport, in terms of percentages, in terms of gain and loss, in terms of supply, in terms of competition, in terms of indirect benefits, etc.) with respect to specific enzyme annotations derived from suitable databases. In examples, enzymes associated with chlorine pathways can include one or more of: chloride channel CLIC-like protein 1, solute carrier family 12 (sodium/potassium/chloride transporter) members, chloride channel protein, CIC family, Ca-activated chloride channel homolog, or other suitable enzymes.

In examples, outputs of Block S130 can include features associated with magnesium pathways (e.g., magnesium transport, in terms of percentages, in terms of gain and loss, in terms of supply, in terms of competition, in terms of indirect benefits, etc.) with respect to specific enzyme annotations derived from suitable databases. In examples, enzymes associated with magnesium pathways can include one or more of: Mg2+-importing ATPase [EC:3.6.3.2], magnesium transporter, putative Mg2+ transporter-C (MgtC) family protein, phosphatidylinositol alpha 1,6-mannosyltransferase [EC:2.4.1.–], magnesium transporter, or other suitable enzymes.

Output features of Block S130 can, however, include other features associated with other micronutrient and/or macronutrient metabolic pathways, some examples of which are described in applications incorporated by reference.

2.2.6 Functional—Plant Growth Promoters (PGPs)

In more detail with respect to generation of features related to plant growth promoters (PGPs), Block S130 can include steps for directly mapping the genera and/or species that result from other annotations (e.g., taxonomic annotations described in related applications and/or applications incorporated by reference) to curated databases of microorganisms. Block S130 can, however, implement other mapping or transformation algorithms for generating features associated with PGPs.

In examples, outputs of Block S130 can include features with respect to specific organism annotations (e.g., in a crop-agnostic manner, in a crop-specific manner) derived from suitable databases, where the features are associated with one or more of: salt tolerance, heavy metal solubilization, indoleacetic acid production, cytokinin production, gibberellin production, ACC deaminase, exopolysaccharide production, abscisic acid, salicylic acid, siderophore production, or other suitable plant growth promoter features.

Output features of Block S130 can, however, include other features associated with other plant growth promoter features, some examples of which are described in applications incorporated by reference.

2.2.7 Functional—Biocontrol Species

In more detail with respect to generation of features related to biocontrol species, Block S130 can include steps for directly mapping the genera and/or species that result from other annotations (e.g., taxonomic annotations described in related applications and/or applications incorporated by reference) to curated databases of microorganisms. Block S130 can, however, implement other mapping or transformation algorithms for generating features associated with biocontrol species.

In examples, outputs of Block S130 can include features with respect to specific organism annotations (e.g., in a crop-agnostic manner, in a crop-specific manner) derived from suitable databases, where the features are associated with one or more of: fungicide biocontrol agents, bactericide biocontrol agents, nematicide biocontrol agents, insecticide biocontrol agents, or other suitable biocontrol agent features (e.g., in terms of abundances represented). Such agents can thus be grouped according to the types of "pests" they encounter and/or capabilities for preventing pathogenic taxonomic groups from proliferating.

Output features of Block S130 can, however, include other features associated with other biocontrol species features, some examples of which are described in applications incorporated by reference.

2.2.8 Functional—Overall Functional Diversity Metrics

In more detail with respect to generation of diversity features with respect to functional annotation, variations of Block S130 can include steps for performing alpha-, beta-, and/or gamma-diversity analyses in relation to various features. For instance, variations of the method include steps for performing alpha- and beta diversity analyses (e.g., derived from 16S and ITS ASV or OTU counts associated with taxonomies and/or functional features), where alpha-diversity metrics (e.g., Shannon, richness, etc.) were calculated and plotted across all covariates available. In relation to various inputs and/or practices, Block S130 can implement architecture for performing tests (e.g., Wilcoxon rank-sum tests) to compare samples associated with different inputs and/or management practices (e.g., control and treatment groups) within various subgroups.

In variations of Block 130, functional diversity analyses can include rarefaction of samples to a common desired sequencing depth (e.g., 100,000 reads, 50,000 reads, 20,000 reads, 10,000 reads, etc.) and replicating the rarefaction a number of times to ensure the results of the subsample are representative of the entire sample (e.g., repeating 10 times, repeating 50 times, repeating 100 times, repeating 500 times, etc.)

For beta-diversity, the Block S130 can implement architecture for determining beta-diversity characteristics. For instance, in one variation, Block S130 includes steps for implementing Kruskal's non-metric multidimensional scaling in conjunction with Aitchison distances. Block S130 can also implement architecture for performing permutational multivariate analysis of variance on the Aitchison distance matrix, using all possible combinations of the location, timepoint and treatment variables.

However, other variations of methods for characterizing diversity metrics and/or other statistical methods can be implemented.

Furthermore, outputs of Block S130 can further implement steps for taxonomic annotation and/or generation of ecological indices as described in related applications, which can be processed individually and/or in combination with functional annotation in relation to generation of agronomic indices in Block S140 below.

2.2.9 Ecological—Resilience Indices

In more detail with respect to generation of features related to resilience, Block S130 can include steps for generating values of resilience indices based upon or otherwise derived from transitivity of bacterial networks and fungal networks. In variations, resilience indices can be determined based upon processing features associated with co-inclusion and co-exclusion factors generated from sample processing and analysis operations described above and/or in U.S. application Ser. No. 17/119,972 filed 11 Dec. 2020.

In particular, in order to generate resilience indices, Block S130 can include generating a network property dataset (e.g., with respect to bacterial networks, with respect to fungal networks, with respect to other organism networks, etc.) from outputs of Blocks S110 and S120, and then processing the network property dataset with architecture for implementing one or more processes including: transforming a first grouping of positive pairs of organisms and a second grouping of negative pairs of organisms (i.e., organisms represented in the sample dataset, related to co-inclusion and co-exclusion, respectively) into one or more aggregate matrices representing co-inclusion parameters (e.g., the whole number of potential associations between all the taxa in the pool, associations that are described as system relevant interdependencies including: biotic interactions, environmental affinities, dispersal restrictions, etc.) and co-exclusion parameters (e.g., for various taxonomic units associated with metacommunities or other communities represented in the set of samples); subdividing the one or more aggregate matrices into a set of individual matrices containing features associated with only the species (or other taxonomic units) occurring in each of the set of samples; performing co-inclusions and/or co-exclusion estimations in a suitable manner (e.g., based upon covariance determination methods, based upon correlation determination methods, with SparCC, with SPIECeasi etc.); processing the set of individual matrices in order to generate a set of undirected network mappings with nodes representing species (or other taxonomic units) and edges representing statistically significant co-inclusions/co-exclusions; and performing other suitable data processing steps.

Then, in relation to Block S130, the computing platform can implement architecture for extracting features associated with transitivity from the set of undirected network mappings, where features can be derived from extraction of interconnections between adjacent and non-adjacent nodes of the network mappings, as a proxy for the tightness of connected communities. Such transitivity features can then be processed in order to generate values of resilience indices associated with the set of samples.

Additionally or alternatively, resilience indices can be generated from features including one or more of: a number of connected components (i.e., defined in relation to a subnetwork in which any two nodes connect to each other by edges, that lack connection to other nodes in the full network); a modularity factor (e.g., a quality of a partition into modules such as groups of nodes using a quantity of edges inside modules compared to a quantity of edges between modules, using an appropriate clustering algorithm (e.g. walktrap, Louvain, fast greedy, edge-betweenness, etc.); a clustering coefficient; an average path length between network components (i.e., defined as a mean of the minimal number of required edges to connect any two nodes); an assortativity factor (e.g., a feature which measures homophyly of a network, according to node properties or labels such as node degree, which quantifies the number of edges associated to a node); a proportion of co-inclusion factor normalized to a total number of combinations of all OTUs/ASVs in the sample(s); a proportion of co-exclusion factor normalized to a total number of combinations of all OTUs/ASVs in the sample(s); and other suitable features.

Resilience indices can then be used to characterize aspects and effects of any input/management practice for any crop, agriculture site, and/or soil type, where the input/management practice alters the structure of microbial communities of the soil, and a decreased transitivity (and thus, resilience) on the network (e.g., fungal network, bacterial network) can indicate such an effect. Resilience index outputs of Block S130 can, however, be derived in another suitable manner, some examples of which are described in applications incorporated by reference.

2.2.10 Ecological—Disease-Risk Associated Functions

In more detail with respect to generation of features related to disease-risk associated functions, Block S130 can include steps for directly mapping the genera and/or species that result from other annotations (e.g., taxonomic annotations described in related applications and/or applications incorporated by reference) to curated databases of microorganisms, and extracting disease risk-associated features accordingly. Block S130 can, however, implement other mapping or transformation algorithms for generating features associated with disease risk in another suitable manner.

In examples, outputs of Block S130 can include features with respect to specific organism annotations (e.g., in a crop-agnostic manner, in a crop-specific manner) derived from suitable databases, where the features are associated with disease risk as disease-risk indices in relation to one or more of rot, scab, wilt, blight, scurf, canker, wart, dot, spot, pit, blotch, rust, gangrene, mold, leak, mildew, smut, or other suitable diseases. Disease risk-associated features can further be associated with any part of any crop. In examples, disease risk-associated features can be generated in association with one or more of: bacterial rot, charcoal rot, common scab, other scab, early blight, *fusarium* dry rot, *fusarium* wilt, late blight, pink eye, pink rot, ring rot, powdery scab, black scurf and stem canker, *verticillium* wilt, wart, black dot, brown spot, black pit, *Cercospora* leaf blotch, *Choanephora* blight, common rust, deforming rust, gangrene, grey mold, leak, *Phoma* leaf spot, *Pleospora herbarum*, powdery mildew, *Rosellinia* black rot, *Septoria* blight, silver scurf, skin spot, stem rot, *Thecaphora* smut, *Ulocladium* blight, white mold, zebra chip disease, or other suitable disease-associated features.

Exemplary disease-risk associated features for soil potatoes can additionally or alternatively include: bacterial soft rot and black leg (e.g., from tubers, associated with *Pectobacterium atrosepticum, Pectobacterium carotovorum*, etc.); bacterial wilt or brown rot (e.g., from leaves, associated with *Ralstonia solanacearum*, etc.); charcoal rot (e.g., from tubers, associated with *Macrophomina phaseolina*, etc.); common scab (e.g., from tubers, associated with *Streptomyces acidiscabies, Streptomyces scabiei, Streptomyces turgidiscabies*, etc.); early blight (e.g., from leaves, stems, and tubers, associated with *Alternaria solani, Macrophomina phaseolina, Fusarium acuminatum*, etc.); *fusarium* dry rot (e.g., from tubers, associated with *Fusarium acuminatum, Fusarium avenaceum, Fusarium culmorum, Fusarium equiseti, Furarium oxysporum, Fusarium solani, Fusarium* sp., etc.); *fusarium* wilt (e.g., from leaves, associated with *Fusarium avenaceum, Fusarium oxysporum, Fusarium solani, Fusarium* sp., etc.); late blight (e.g., from leaves, stems, tubers, associated with *Botrytis cinerea, Pseudomonas fluorescens, Phytopthhora cryptogea*, etc.); pink eye (e.g., associated with Pseudomona florescens, etc.); pink rot (e.g., associated with *Phytophthora drechsleri, Phytophthora megasperma, Phytophthora nicotianae, Phytophthora* sp., etc.); ring rot (e.g., associated with *Clavibacter* michiganesis, etc.); powdery scab (e.g., from tubers, associated with *Spongospora subterranea*, etc.); black scurf stem canker (e.g., from tubers, associated with *Rhizoctonia solani*, etc.); *verticillium* wilt (e.g., from roots, stems, and leaves, associated with *Verticillium albo-atrum, Verticillium dahliae*, etc.); wart (e.g., from tubers, associated with *Synchytrium endobioticum*, etc.); black dot (e.g., from tubers, associated with *Colletotrichum agaves*, etc.); brown spot and black pit (e.g., associated with *Alternaria alternata*, etc.); *Cercospora* leaf blotch (e.g., associated with *Cercospora solani*, etc.); *Choanephora* blight (e.g., associated with *Choanephora cucurbitarum*, etc.); common rust (e.g., associated with *Puccinia pittieriana*, etc.); deforming rust (e.g., associated with *Aecidium cantensis*, etc.); gangrene (e.g., associated with *Boeremia foveata, Phoma exigua*, etc.); gray mold (e.g., associated with *Botrytis cinerea*, etc.); leak (e.g., associated with *Pythium aphanidermatum, Pythium deliense, Pythium* sp., *Pythium ultimum*, etc.); phoma leaf spot (e.g., associated with *Phoma andigena*, etc.); *Pleospora herbarum* (e.g., associated with *Phoma andigena*, etc.); *Pleospora herbarum* (e.g., associated with *Ploespora herbarum*, etc.); powdery mildew (e.g., from leaves, associated with Colovinomyces *cichoracearum*, etc.); *Rosellinia* black rot (e.g., associated with *Rosellinia* sp., etc.); *Septoria* blight (e.g., associated with *Septoria* lycoperisici, etc.); silver scurf (e.g., associated with *Helminthosporium solani*, etc.); skin spot (e.g., associated with *Polyscytalum pustulans*, etc.); stem rot (e.g., associated with *Sclerotium rolfsii*, etc.); *Thecaphora* smut (e.g., associated with *Thecaphora solani*, etc.); *Ulocladium* blight (e.g., associated with *Ulocladium atrum*, etc.); white mold (e.g., associated with *Sclerotinia sclerotiorum*, etc.); zebra chip disease (e.g., from tubers, associated with Liberibacter *solanacearum*, etc.); and/or other factors.

Output features of Block S130 can, however, include other features associated with other disease-associated features, some examples of which are described in applications incorporated by reference.

2.2.11 Ecological—Impact

In more detail with respect to generation of features related to impact-associated features, Block S130 can include steps for generation of impact-associated ecological indices based upon bacteria-associated parameters and fungal-associated parameters, and then processing such network property parameters to generate features (e.g., as a unified "impact" parameter or feature), as another proxy for resilience/resistance of a soil microbiome community in relation to responses to various disease risks (described above). The impact parameter can represent a change in the co-occurrence and co-exclusion among microorganisms (e.g., changes in co-occurrence and co-exclusion of bacterial and fungal organisms represented in the sample dataset), where methods of generating co-occurrence and co-exclusion parameters are described in U.S. application Ser. No. 17/119,972 filed 11 Dec. 2020 and incorporated by reference above. In variations, the impact parameter can be determined based upon aggregation of all co-occurrence network properties and all co-exclusion network properties into a value that summarizes the effect that treatment or management practices has at each location.

For instance, an impact parameter can be derived from the distances (e.g., as a measure of dissimilarity) between the network properties (e.g., 16S network properties, ITS network properties) as a measure of the effect of a given input (e.g., treatment, management practice, product, etc.) on the bacterial and fungal network properties of the soil from one location. A linear regression model can be used to model the network properties, using location and timepoint only. The residuals of these models can then be projected onto a multidimensional space (e.g., using principal component analysis (PCoA)).

In a specific example, an impact parameter characteristic of resilience can be derived from the scaled dissimilarity (distance) between the network properties (e.g., 16S network properties, ITS network properties) of treated and control samples in a given location, as a measure of the effect of a given input or practice (e.g., treatment, management practice, product, etc.) on the bacterial and fungal network properties of the soil from one location. A linear regression model can be used to model the network properties, using location and timepoint only. The residuals of these models are then projected onto a 10-dimensional space using principal component analysis (PCoA), retaining 83% of variation in the residuals. In more detail, a method for determining impact parameters can include: modelling network properties from samples, using desired contextual parameters (e.g., location, time point), with collection of residuals; running a PCoA on these residuals and generate a multi-dimensional location for each sample; and calculating the distance between the treatment and control centroids. For each location, the impact parameter is the weighted distance between treated and control samples of that location. Impact parameter values are thus distances (i.e. non-negative), and an impact parameter value of zero means that the treatment had negligible effect on the network properties of the soil microbiome. Furthermore, the magnitude of the impact parameter correlates with the magnitude of the effect of the particular input/practice.

Output features of Block S130 can, however, include other features associated with other resilience-associated features, some examples of which are described in applications incorporated by reference.

2.2.12 Ecological—Sustainable Productivity Index

Additionally or alternatively, the invention(s) can generate and apply a sustainable productivity index score. In embodiments, the sustainable productivity index score is crop-agnostic, using network properties and principal components of taxonomy and combining them to generate a single score. In variations, the sustainable productivity index can use microbiome functional annotations and/or other suitable annotations.

In embodiments, the sustainable productivity index can be defined based upon a proprietary database of soil samples from diverse crops with known management practices, where an increasing order of sustainability is defined based upon a set of predetermined management practices (e.g., conventional, organic and biodynamic). In embodiments, the system can include architecture for generating, training, and applying a combined supervised machine learning model, including regression and classification tasks to compute the index. In variations, the regression model can be constructed to predict a pre-score following expert-based criteria regarding management practices distances. In variations, the classification model can be constructed apply a management-dependent transformation over the pre-score. In examples, the sustainable productivity index quantitative values are in the range 0 to 100, going from lower to higher soil sustainability or productivity. In examples, the sustainable productivity index qualitative categories are in the range "infertility risk" to "natural farming", going from lower to higher soil sustainability or productivity.

In embodiments, the sustainable productivity index machine learning model can be applied to determine the score for any new/incoming soil sample, based upon one or more microbiome-derived properties defined above.

2.2.13 Overall Combinatorial Metrics

Furthermore, outputs of Block S130 can further implement steps for generation of combinatorial metrics based upon taxonomic annotations, functional annotations, and/or ecological indices generated as described above and/or in another suitable manner, which can be processed individually and/or in combination with other annotations and/or markers in relation to generation of agronomic indices in Block S140 below.

2.2.14 Refinement and Training

In relation to model architecture associated with training and refinement of machine learning models described, methods described in relation to Blocks S120 and S130 can be used to create training sets of data. As such, training data covering specific sample features and corresponding contextual information related to management practices and other perturbations (e.g., use of various products, environmental perturbations, other agricultural inputs, other practices, etc.) can be used to refine models for predicting effects of various practices and perturbations, and to guide future management practices in a sustainable manner.

In order to process such data, computing platforms implementing one or more portions of the method can be implemented in one or more computing systems, wherein the computing system(s) can be implemented at least in part in the cloud and/or as a machine (e.g., computing machine, server, mobile computing device, etc.) configured to receive a computer-readable medium storing computer-readable instructions.

To refine the model(s), the method 100 can include generating one or more training sets of data, from samples of the agriculture site(s) and/or other samples of other agriculture site(s), in order to train the artificial intelligence (AI)/neural network (NN) model(s) in one or more stages of training, to identify features of interest from various inputs. In variations, generating training sets of data can include processing raw data and/or features taken from agriculture sites and/or crops with known characteristics (e.g., in relation to contextual and/or other data described above, in relation to agricultural inputs/practices applied in substantially controlled settings, etc.). Such training data can be tagged with associated crop-associated features, agriculture site statuses (e.g., health statuses) and/or other information (e.g., pertaining to nature of inputs/practices, etc.).

In examples, training data can include tagged contextual information, which can include environmental information, geolocation information, nature of products applied (e.g., dosing, duration of application, frequency of application), pathogens present at a site, and/or other suitable information.

Training sets of data can include raw sequencing data, transformed sequencing data (e.g., according to transformation operations described above), and/or other suitable data. As such, as shown in FIG. 3, the method 100 can include: generating one or more training datasets S145 from a set of agriculture sites and/or crops (e.g., sites different from those in step S110, sites overlapping with those in step S110), the training datasets corresponding to features (e.g., of taxonomic annotations, of functional annotations, of ecological indices, etc.) in association with statuses and/or inputs or practices experienced by the agriculture site(s) and associated crops; applying one or more of a set of transformation operations to the one or more training datasets (e.g., using one or more operations described above) S146; and training a machine learning model comprising architecture for returning at least one of the set of unique signatures and the analysis, in one or more stages, based upon the one or more training datasets S147. Additional details are provided below.

For instance, in relation to generation of training datasets, the method can include generating taxonomic annotations, functional annotations, ecological indices, agronomic indices and other features upon samples from agriculture sites (or other sites) where statuses and/or perturbations are known. Additionally or alternatively, first training datasets can be generated from network properties/emergent properties and other features upon processing samples from agriculture sites (or other sites) known to be at baseline state. The model can be trained based upon the first training datasets. Then, the site(s) and/or associated crops can be intentionally perturbed in some manner, with subsequent sample acquisition and processing used to generate second training datasets for refining the model. This process can be repeated any suitable number of times. As such, training data can be developed in multiple stages. In relation to multiple stages of training, the method 100 can refine models based upon incorrect classification of outputs (e.g., mis-characterized statuses and/or perturbations).

Furthermore, combinatorial features (e.g., combination features derived from one or more individual network properties, one or more community properties, one or more taxonomic properties, and/or other suitable properties) can be used for training. In more detail, features may be transformed either individually or in combination before being processed by the model(s). As an example of an individual feature transformation, a feature derived from a transform of a co-exclusion feature might be used instead of or in addition to the co-exclusion feature itself. As an example, a combinatorial feature can be derived from synchronous co-exclusion of a pair of organisms and co-inclusion of a pair of organisms (e.g., where occurrence together is a feature). Additionally or alternatively, combinatorial features based upon bacteria-associated parameters and fungal-associated parameters can be used as inputs (e.g., as a unified "impact" parameter or feature). For instance, an impact parameter can be derived from the scaled dissimilarity (distance) between the network properties (e.g., 16S network properties, ITS network properties), as described in U.S. application Ser. No. 17/119,972 filed n-DEC-2020, incorporated by reference above.

Additionally or alternatively, dynamic aspects (e.g., changes over time in features, changes in frequency between instances of respective features, other temporal aspects, other frequency-related aspects, etc.) of features derived from the samples can be used to predict or otherwise anticipate statuses. As such, models can be implemented to prevent adverse statuses of the agriculture sites to prevent root causes of failure and/or break chains of events that could lead to a cascade of agriculture site problems.

Models can be developed and trained for real-time analyses and/or historical analyses. In relation to real-time analyses, the models can be refined for rapid classification (e.g., with node reduction, with reduced thresholds, with lower confidence, etc.). In relation to historical analyses, the models can be refined for detailed classification (e.g., without node reduction, with higher thresholds for classification predictions, with higher confidence, etc.).

In embodiments, the method 100 can thus include training a model configured to process input features and return predicted characterizations of agronomic indices and/or associated features of the agriculture site, wherein training the model comprises: collecting a training dataset derived from samples, the training dataset corresponding to training samples subject to at least one of a management practice and a perturbation (e.g., substance applied, environmental control condition, etc.) at the agriculture site as well as control samples without undergoing the input factor; applying one or more of a set of transformation operations to the training dataset; and training the model with the training dataset, the model comprising architecture for returning the analysis, in one or more stages. Training and refinement can be further applied to outputs for generation of agronomic indices and recommended actions, as described in further detail below.

While embodiments, variations, and examples of models (e.g., in relation to inputs, outputs, and training) are described above, models associated with the method can additionally or alternatively include other blocks for statistical analysis of data and/or machine learning architecture.

Statistical analyses and/or machine learning algorithm(s) can be characterized by a learning style including any one or more of: supervised learning (e.g., using back propagation neural networks), unsupervised learning (e.g., K-means clustering), semi-supervised learning, reinforcement learning (e.g., using a Q-learning algorithm, using temporal difference learning, etc.), and any other suitable learning style.

Furthermore, any algorithm(s) can implement any one or more of: a regression algorithm, an instance-based method (e.g., k-nearest neighbor, learning vector quantization, self-organizing map, etc.), a regularization method, a decision tree learning method (e.g., classification and regression tree, chi-squared approach, random forest approach, multivariate adaptive approach, gradient boosting machine approach, etc.), a Bayesian method (e.g., naïve Bayes, Bayesian belief network, etc.), a kernel method (e.g., a support vector machine, a linear discriminant analysis, etc.), a clustering method (e.g., k-means clustering), an associated rule learning algorithm (e.g., an Apriori algorithm), an artificial neural network model (e.g., a back-propagation method, a Hopfield network method, a learning vector quantization method, etc.), a deep learning algorithm (e.g., a Boltzmann machine, a convolution network method, a stacked auto-encoder method, etc.), a dimensionality reduction method (e.g., principal component analysis, partial least squares regression, etc.), an ensemble method (e.g., boosting, boot strapped aggregation, gradient boosting machine approach, etc.), and any suitable form of algorithm.

2.3 Methods—Generating Agronomic Indices

In Block S130, generating the set of microbiome-associated features can further include generating values of a set of agronomic indices based one or more of the taxonomic annotation(s), functional annotation(s), and/or ecological indices described, which functions to transform outputs into features falling into one of multiple (e.g., three) "agronomic" categories: biosustainability, health, and nutrition. Outputs can be returned in relation to quantitative values and/or qualitative values (e.g., based upon the quantitative values). In an example, quantitative values can be transformed to a qualitative scale of 5 quintiles: very low, low, medium, high, very high. However, output values of the agronomic indices can be provided in another suitable manner.

2.3.1 Agronomic Indices: Biosustainability

1. Biosustainability: In examples, the invention(s) can generate and implement multiple (e.g., 3, less than 3, more than 3) metrics characterizing diversity of sample species and/or metabolic functions present in the sample(s) from the agricultural sites, as well as vulnerability of the system based on estimation of microbiome resistance. Biosustainability indices are biomarkers of the ecosystem in which a site is based, and related to management practices. In examples, three biosustainability indices can be generated:

1A. Biodiversity (species richness, evenness, and equilibrium of species): outputs can be generated from Shannon diversity characterization, based on taxonomic assignment. However, other outputs can additionally or alternatively be generated based upon evaluation of richness, phylogenetic entropy (e.g., based on a proprietary database of soil samples), or any other method(s).

1B. Functionality (capability of communities to perform one or more functions): outputs can be generated from Shannon diversity of the metagenomic functions predicted, but it could be any other diversity metric based on the functions.

1C. Resistance (stress adaptation, ability of communities or populations to remain unchanged when stressed by a disturbance): outputs can be generated from the transitivity of the bacterial network, but again could be any other suitable network property. Exemplary species grouped according to their relationship with metabolisms associated with capability to withstand stress conditions include: Exopolysaccharide production capabilities (e.g., with nutrient trapping capabilities, salinity protection capabilities, drought protection capabilities, etc.); heavy metal solubilization (e.g., with bioremediation capabilities, detoxification capabilities, heavy metal stress alleviation capabilities, etc.); salt tolerance capabilities (e.g., with salinity protection capabilities, root growth promotion capabilities, etc.); siderophore production capabilities (e.g., with association iron availability, biofertilizer capabilities, etc.); ACC deaminase capabilities (e.g., with pathogen protection capabilities, with salinity protection capabilities, with drought protection capabilities, etc.); salicylic acid capabilities (e.g., with drought protection capabilities, with salinity protection capabilities, with heavy metal stress alleviation capabilities, etc.); abscisic acid production (e.g., with growth regulation capabilities, with plant resistance capabilities, with yield increase capabilities, etc.).

In examples, low value indices are indicators of aggressive practices, while high value indices are linked to sustainable practices.

As such, generating values of the biosustainability index can include generating a biodiversity value representing species richness, a functionality value representing metagenomic functions, and a resistance value representing stress adaptation of communities represented in the sample dataset.

2.3.2 Agronomic Indices: Health

2. Health: In examples, the invention(s) can generate and implement multiple (e.g., 4) metrics characterizing the role of microorganisms in plant health and yield, as defined by a balance between pathogens, biocontrol agents, and/or other plant growth promoters:

2A. Healthiness (crop health according to detected pathogens): In examples, the invention(s) include steps for generating a score for each disease-risk factor based on the crop-specific pathogen lists. The score (quintile) combines the relative abundance of the disease-risk factor and the resistance score of the soil. Then, based on the quintiles of the minor and major diseases per crop, the invention(s) include architecture for calculating a health score as follows:

At least one major disease in sample at level 5 (maximum quintile), then score=1.

At least one major disease in sample at level 4, then score=2

At least one major disease in sample (not zero), then score=3

At least one minor disease in sample (not zero), then score=4 no disease in sample, then healthiness score=5

In addition to just using the resistance score (i.e., based upon transitivity of networks described above), the invention(s) can further implement transitivity of fungal networks, and co-exclusion proportions in both (bacterial & fungal) networks. Additionally or alternatively, the invention(s) can generate and apply a health index score that is crop-agnostic (i.e. not using disease abundances, but instead, using network properties and principal components of taxonomy and combining them to generate a single score, examples of which are defined above in embodiments, variations, and examples, and further shown in applications incorporated by reference.

In further variations, the invention(s) can be applied to soils known to suppress certain diseases in contrast to soils that allow the diseases to occur, thereby enabling identification of specific taxa or network properties that explain the suppression of the disease pathogens.

In variations, health indices (e.g., soil health indices) can be generated from samples having known management practices (e.g., conventional, organic, biodynamic, etc.), from a wide variety of geographies and crop types (e.g., almond, banana, corn, horticolas, lettuce, mustard, olive, onion, peppers, pimentos, rapeseed, tomatoes, vineyard, wheat, other, etc.). In examples, the dataset generated from samples was split into training and test datasets, and the data was modeled (e.g., using a LASSO Ridge regression, using 16S and ITS data, enriched and depleted, network properties), thereby generating coefficients for modularity, transitivity, assortativity, p-length, and other properties. Coefficients represent the amount by which the health index increases/decreases when a given variable increases by one standard deviation, and can be tagged to indicated interactions between different variables.

Variations of models can include accounting for network properties and principal components from taxonomic annotation (e.g., to improve model fit), where health indices can be divided categorically (e.g., in ranges), characterizing 16S+ITS, 16S only, and ITS only. As such, models for generating and returning health index values based upon features generated in Block S120 can be constructed to inform actions executed in Block S150.

In relation to health indices, the method can further include generation of sustainable productivity indices as a proxy for health, where the sustainable productivity indices can be generated as described and/or in applications incorporated by reference.

2B. biocontrol species (microbial species grouped according to the type of pests they encounter, capability of preventing pathogenic species from taking hold or proliferating): The invention(s) can generate relative abundances of the microorganisms on each of these categories: Fungicides, Bactericides, Insecticides, and Nematicides. Additionally or alternatively, the invention(s) can process and apply network properties, since a soil with a high fungal network transitivity and a strong biocontrol set of species is going to be even more resilient to external disruptions (e.g., abiotic, biotic, etc.) than one with just the biocontrol species present but not a high network transitivity.

2C. phytohormone producing species (microbial species grouped according to the type of phytohormone they generate): The invention(s) include steps and architecture for generating relative abundance of microorganisms that produce: Cytokinin production (e.g., with cell proliferation hormone generation, with cell differentiation hormone generation, etc.), Auxin production (e.g., with cell division hormone generation, with stem elongation hormone generation, etc.), and Gibberellin production (e.g., with stem elongation hormone generation, with germination hormone generation, with flowering hormone generation, etc.) for instance, in terms of percentages).

2D. stress sensing and tolerance species (microbial species grouped according to their ability to produce metabolites that help plants withstand stress conditions): The invention(s) include steps and architecture for relative abundance of microorganisms that produce: ACC deaminase, exopolysaccharide production, heavy metal solubilization, salt tolerance, siderophore production, salicylic acid, and abscisic acid.

As such, generating values of the health index can include generating a healthiness value associated with detected pathogens, a biocontrol value representing capability of preventing pathogenic species effects at the agriculture site, a phytohormone value representing generated phytohormones, and a stress value representing metabolites associated with stress withstanding.

2.3.3 Agronomic Indices: Nutrition

3. Nutrition: The invention(s) include steps and architecture for characterizing the potential of soil microorganisms to cycle nutrients and to increase the bioavailability of nutrients for plants). Examples of relative abundance of enzymes from predicted metagenomes are described in applications incorporated by reference.

Additionally or alternatively, the inventions can include steps and architecture for processing and applying features related to one or more of:

Carbon (as the basis of soil fertility with release of nutrients for plant growth, promotion of structure and health of soils, and buffer against harmful substances): with identification of new enzyme activities/taxa associated to the potential to sequester carbon. In examples, samples from biodynamic soils (e.g., with no-tilling) with high capacity to sequester carbon, and from traditional soils (e.g. tilling) with low capacity to sequester Carbon, can be processed according to the invention(s) described.

Any nutrient: by determining metabolic fluxes, not just relative abundances of enzyme activities; by determining percentage of enzymes present from a given pathway (not just abundance); by determining function representation in microorganisms from each of the modules in networks. For instance, indices can be related to one or more of: pathways that directly benefit plant nutrition, pathways that take up nutrients from the soil, nitrogen pathways, phosphorus pathways, minor compounds (e.g., sulfur, calcium, chlorine, magnesium, iron, manganese, zinc, copper, and/or other nutrients.

As such, generating values of a nutrition index can include generating values of nutrient dynamics represented in the sample dataset.

In further examples, outputs of the invention(s) can be combined, presented, and/or applied in relation to physicochemical properties of samples or crops, to return biology indexes and physical/chemical indexes, an example of which is shown in applications incorporated by reference.

2.4 Methods—Returned Analyses and Generation of Comparisons for Determining Evolution of Properties Over Time Block S140 recites: returning an analysis of a set of parameters derived from the set of microbiome-associated features. Block S150 recites: generating a set of comparisons between values of the set of parameters associated with the first treatment state and the second treatment state (e.g., control state), across the set of time points. Block S140 functions to return analyses which can be used to assess the effects of treatments for each of the one or more agriculture sites. Comparisons associated with Block S150 can be determined with respect to comparisons between changes in property over time for treatment groups and control groups.

In variations, outputs of Block S140 can include returning analyses characterizing diversity evolution (e.g., with respect to alpha diversity parameters associated with Block S130); microbiome composition evolution (e.g., with respect to beta-diversity parameters from Block S130); agronomic indices evolution (e.g., with respect to evolution of taxonomic markers associated with disease risk, biocontrol, and other factors; with respect to evolution of functional markers associated with macro and micro-nutrient pathways, plant growth promoters, and other factors; with respect to evolution of ecological markers with respect to impact parameters and other network/emergent properties; etc.).

Blocks S140 and S150 include generating analyses on the basis of comparing treatment groups relative to respective control groups, and comparing different sampling times (T1, T2, . . . , Tn) with a time of origin (T0). The value obtained for each feature is then the attributable change that the product or practice of interest causes in samples of the treatment group, and accounts for the natural variation that occurs in the control samples. In generating outputs, Blocks S140 and S150 implement a robust differential expression framework that employs a quasi-likelihood generalized linear model (GLM) framework. Outputs can be represented in terms of percentage changes (e.g., decreases, increases) in a particular value, significant differences between values over time, distances between centroids of parameters corresponding to groups of samples in beta diversity analyses (e.g., with respect to changes in composition of organisms), in relation to ecological change in microbiome communities between groups of samples being compared, with respect to Q-values, and/or in another suitable manner.

2.4.1 Diversity Evolution

In variations, analyses of Block S140 and comparisons of Block S150 can be used to determine evolution of biodiversity, with respect to alpha-diversity characteristics.

Figure 2A:
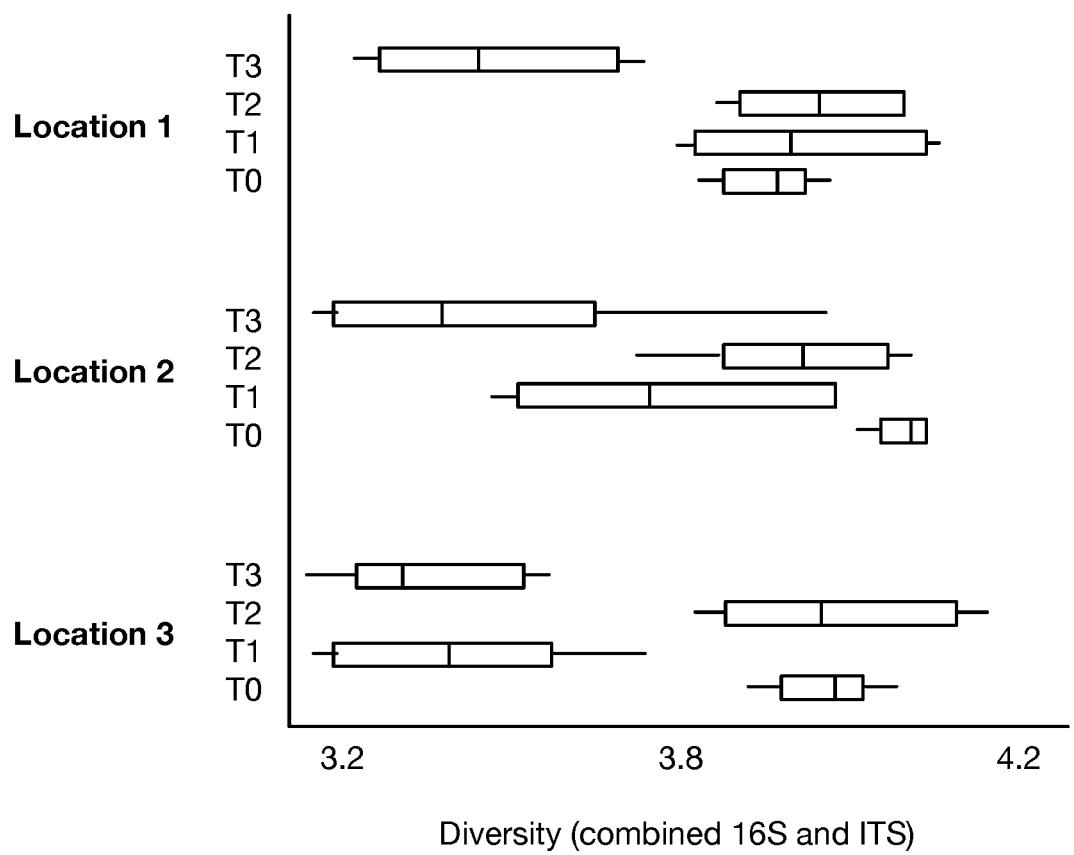
FIGS. 2A and 2B depict example outputs related to changes in diversity across locations and time points with respect to treatments and controls, in accordance with methods and systems for assessing agriculture practices and inputs.
Figure 2B:
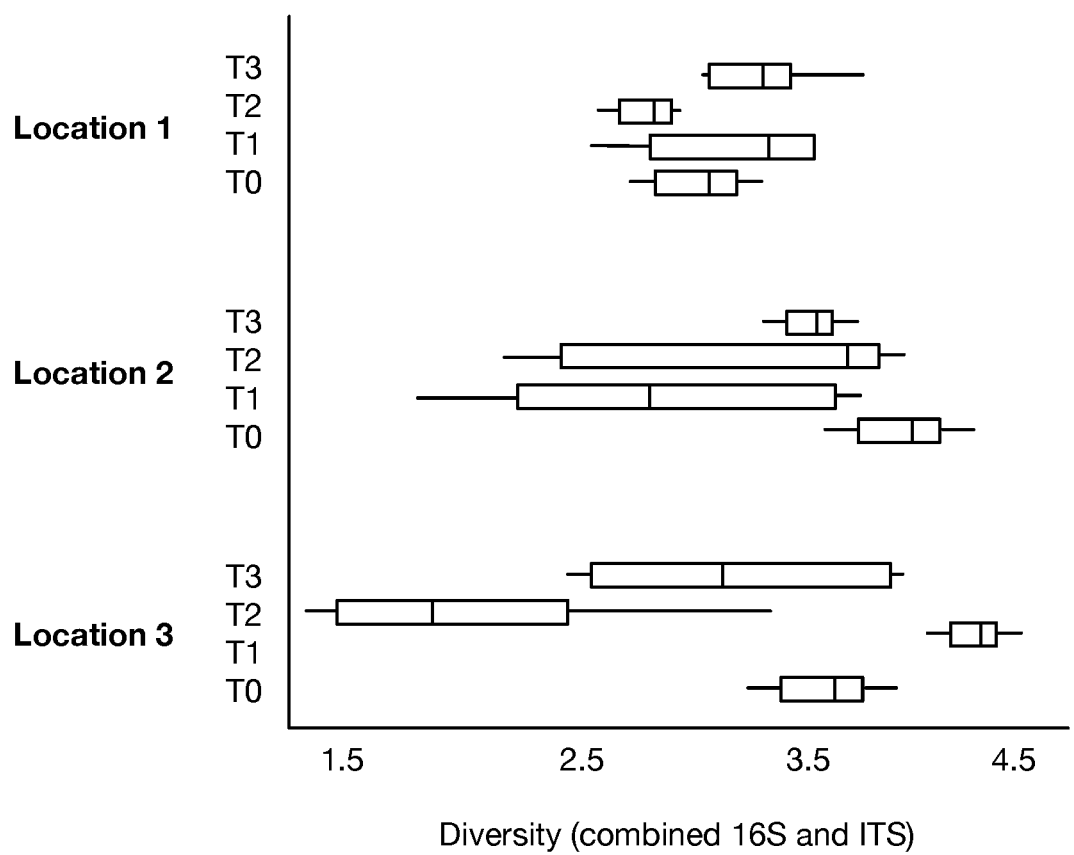

FIGS. 2A and 2B depict comparisons of distributions (e.g., with respect to Shannon diversity) of microbial communities of bacteria (16S) and fungi (ITS), respectively, according to treatment and time point, which can be used to assess effects of the treatment(s). In particular, diversity changes at various time points can be correlated with applied treatments, to assess potential effects of treatments on diversity of soil microbiome communities. Diversity evolution can further be characterized for each location separately, as well as globally across all locations.

However, variations of biodiversity evolution and associated comparisons can be determined in another suitable manner.

Furthermore, analyses returned using Blocks S140 and S150 can further describe the evolution of specific taxa (e.g., of bacteria, of fungi, etc.) with respect to differential abundances at different time points and/or different locations, with respect to treatment and control plots. Evolution of specific taxa can be provided at the species level, the genus level, OTU level, ASV level, and/or at any other suitable taxonomic level.

2.4.2 Composition Evolution

In variations, analyses of Block S140 and comparisons of Block S150 can be used to determine evolution of microbiome composition, with respect to beta-diversity characteristics.

Figure 3A:
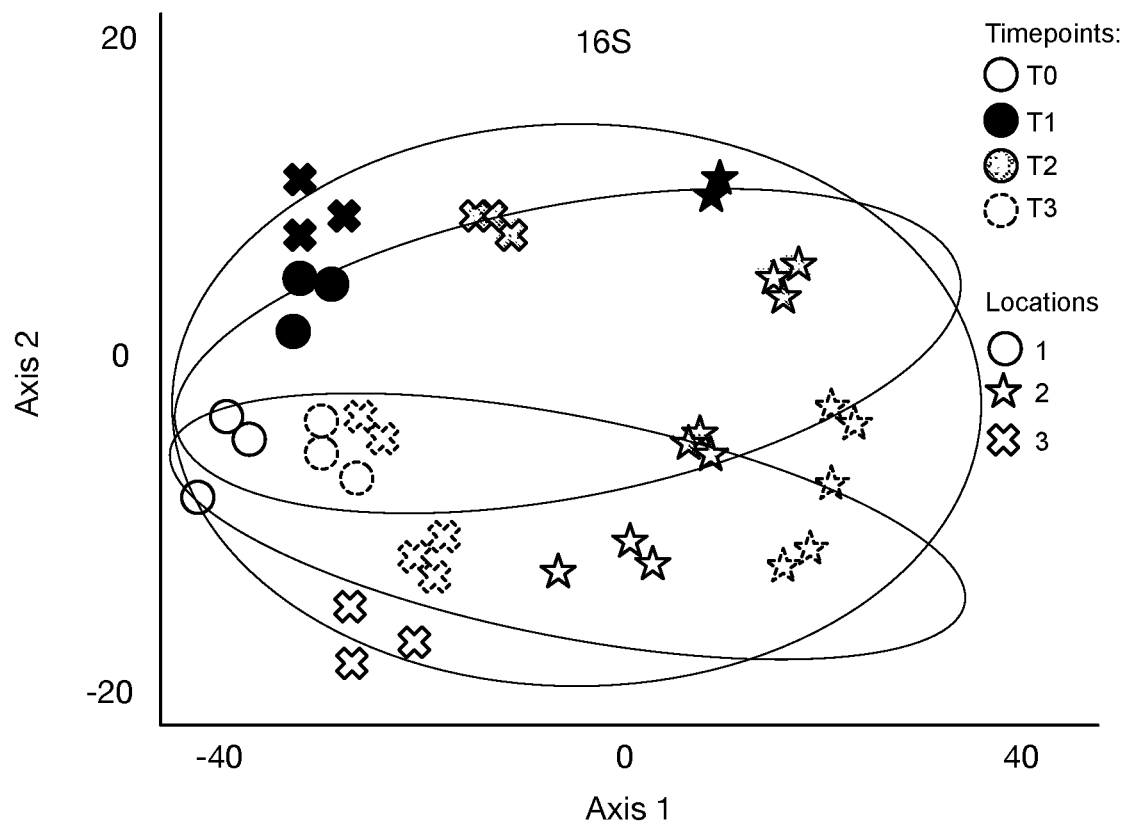
FIGS. 3A and 3B depict example outputs related to changes in composition across locations and time points with respect to treatments and controls, in accordance with methods and systems for assessing agriculture practices and inputs.
Figure 3B:
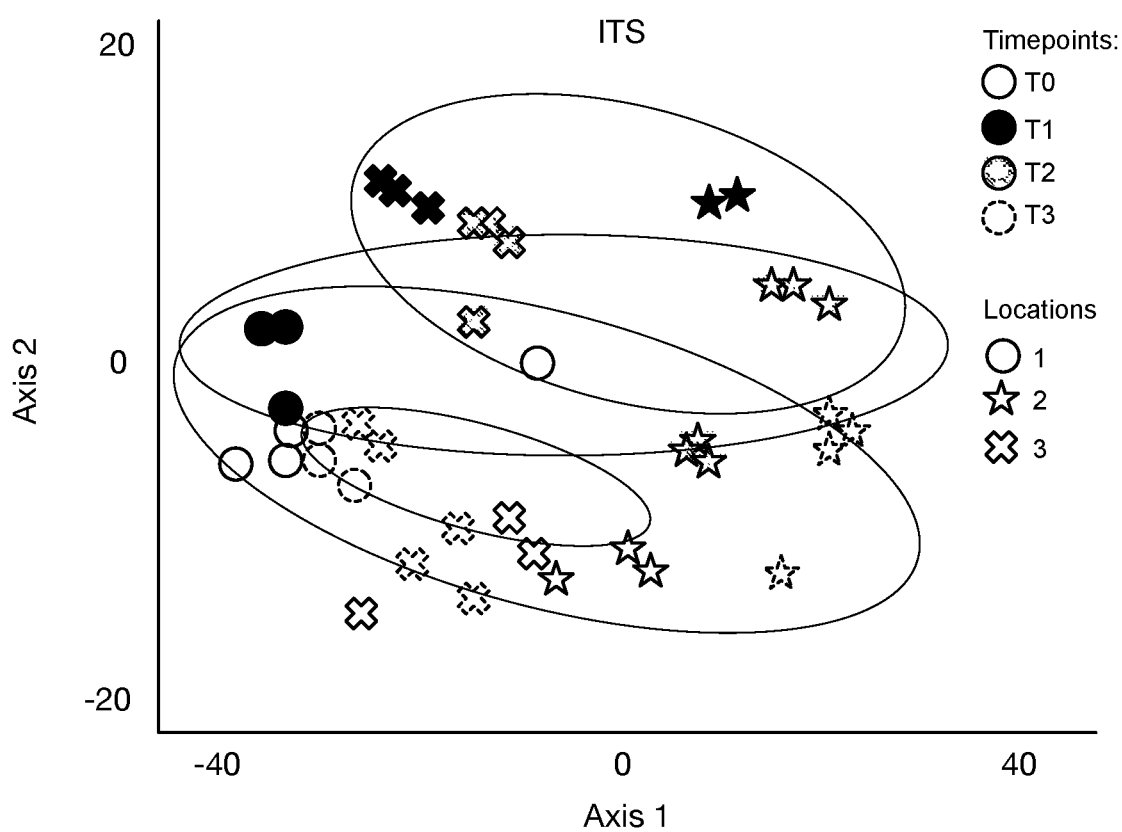

FIGS. 3A and 3B depict comparisons of compositions of microbial communities of bacteria (16S) and fungi (ITS), respectively, according to treatment and time point, which can be used to assess effects of the treatment(s). In particular, compositional changes at various time points can be correlated with applied treatments, to assess potential effects of treatments on composition of soil microbiome communities. Composition evolution can further be characterized for each location separately, as well as globally across all locations.

However, variations of biodiversity evolution and associated comparisons can be determined in another suitable manner.

2.4.3 Agronomic Indices and Evolution

Block S140 can include generation of agronomic indices based on the set of microbiome-associated features, which functions to transform outputs of Block S130 into features falling into one of multiple (e.g., three) "agronomic" categories: biosustainability, health, and nutrition. Outputs can be returned in relation to quantitative values and/or qualitative values (e.g., based upon the quantitative values). Evolution of the agronomic indices over treatment and control groups, across time points and locations, can then be determined based upon the comparisons of Block S150. Blocks S140 and S150 can thus implement quasi-likelihood testing to measure fold changes in taxonomic, functional and ecological biomarkers in treated vs. control samples over time (i.e., ΔTreated/ΔControl). Blocks S140 and S150 can implement proprietary transformations of relative abundance data and other data, with unsupervised batch-effect correction to characterize treatment effects.

Comparisons of Agronomic indices can be used to assess treatment effects.

FIG. 4A depicts an example output of Blocks S140 and S150, with respect to major nutrient pathways, with comparisons between carbon cycle pathways (e.g., carbon fixation, fermentation, organic matter degradation, aerobic respiration, methanogenesis, etc.) nitrogen cycle pathways (e.g., inorganic cycle health, organic nitrogen formation, organic nitrogen degradation, etc.), phosphorus pathways (e.g., inorganic assimilation, organic assimilation, solubilization, etc.), and potassium pathways (e.g., uptake, solubilization, etc.) between each time point assessed. In particular, such outputs can characterize increasing trends associated with major nutrient pathways (e.g., carbon, potassium uptake, etc.), decreasing trends associated with major nutrient pathways (e.g., nitrogen, phosphorus competition, etc.), or no change associated with major nutrient pathways.

FIG. 4B depicts an example output of Blocks S140 and S150, with respect to minor nutrient pathways, with comparisons between iron assimilation, zinc transport equilibrium, manganese transport equilibrium, sulfur cycle equilibrium, calcium transport, copper transport, chlorine transport, magnesium uptake between each time point assessed. In particular, such outputs can characterize trends associated with bioavailability of micronutrients (e.g., increasing bioavailability of iron, zinc, calcium, chlorine, copper, magnesium, etc.).

FIG. 4C depicts an example output of Blocks S140 and S150, with respect to phytohormone evolution (e.g., cytokinin production, auxin production, gibberellin production, etc.), stress adaptor evolution (e.g., ACC deaminase, EPS production, heavy metal solubilization, salt tolerance, siderophore production, salicylic acid, abscisic acid, etc.), and biocontrol agent evolution (e.g., fungicide agent, insecticide agent, nematicide agent, bactericide agent, siderophore production, etc.) over time. In particular, such outputs can characterize trends associated with microorganisms involved in stress adaptation, trends associated with biocontrol organisms, and/or trends associated with phytohormone producers.

FIG. 4D depicts an example output of Blocks S140 and S150, with respect to evolution of disease risk. In particular, such outputs can characterize trends associated with risk of various diseases (e.g., albinism, spots, rot, anthracnose, blight, damping-off, wilt, mold, fruit drop, gummosis, etc.) associated with the crop(s) being analyzed.

Outputs of Blocks S140 and S150 can further include analyses of "universal" commonalities across locations, which can be used to generate science-backed functional claims and marketing claims regarding products associated with the treatment(s) being assessed. Such outputs can be used to highlight benefits of a particular product over non-treatment and/or treatment by a competing product.

2.5 Methods—Actionable Outcomes

In some variations, the method 100 can additionally or alternatively include Block S160, which recites: executing an action for producing a desired outcome in relation to the agriculture site, with respect to one or more specific soil types and/or one or more specific crops, based upon the set of comparisons. Block S160 functions to process outputs of prior steps in order to generate insights and/or execute actions that can improve productivity, correct issues, and/or increase sustainability of practices at the agriculture site(s) being assessed. In particular, agricultural inputs and management practices can have inconsistent field performance with uninformed application, where, in relation to some inputs, different strains and species can have different functional performance under specific environmental and ecological conditions. As such, Block S160 can execute application of and/or modification of agricultural inputs and implement management practices in an informed manner that is targeted to specific crops, soil types, and/or environmental conditions.

In variations, executing the action can include generating digital objects encoding instructions for controlling apparatus associated with an operator managing the agriculture site. In variations, executed actions can include or be associated with one or more of: maintaining a status of an agriculture site by providing guidance for maintaining current management statuses and/or products used; responding to an issue detected at the agriculture site(s) being assessed (e.g., in relation to pathogen presence or increased abundance of a detrimental microorganism, in relation to decreased abundance of a beneficial microorganism, in relation to correcting a perturbation, in relation to adjusting application of a product at the agriculture site, implementing protective measures against environmental effects, etc.); responding to or otherwise correcting other undesired statuses at one or more agriculture sites being monitored; providing information regarding site characteristics to a manager/operator/other entity associated with the agriculture site(s); performing decision-making guidance (e.g., in relation to analyses indicative of sustainability of practices, in relation to long term effects of use of one or more products, etc.); and performing other suitable actions.

Figure 6:
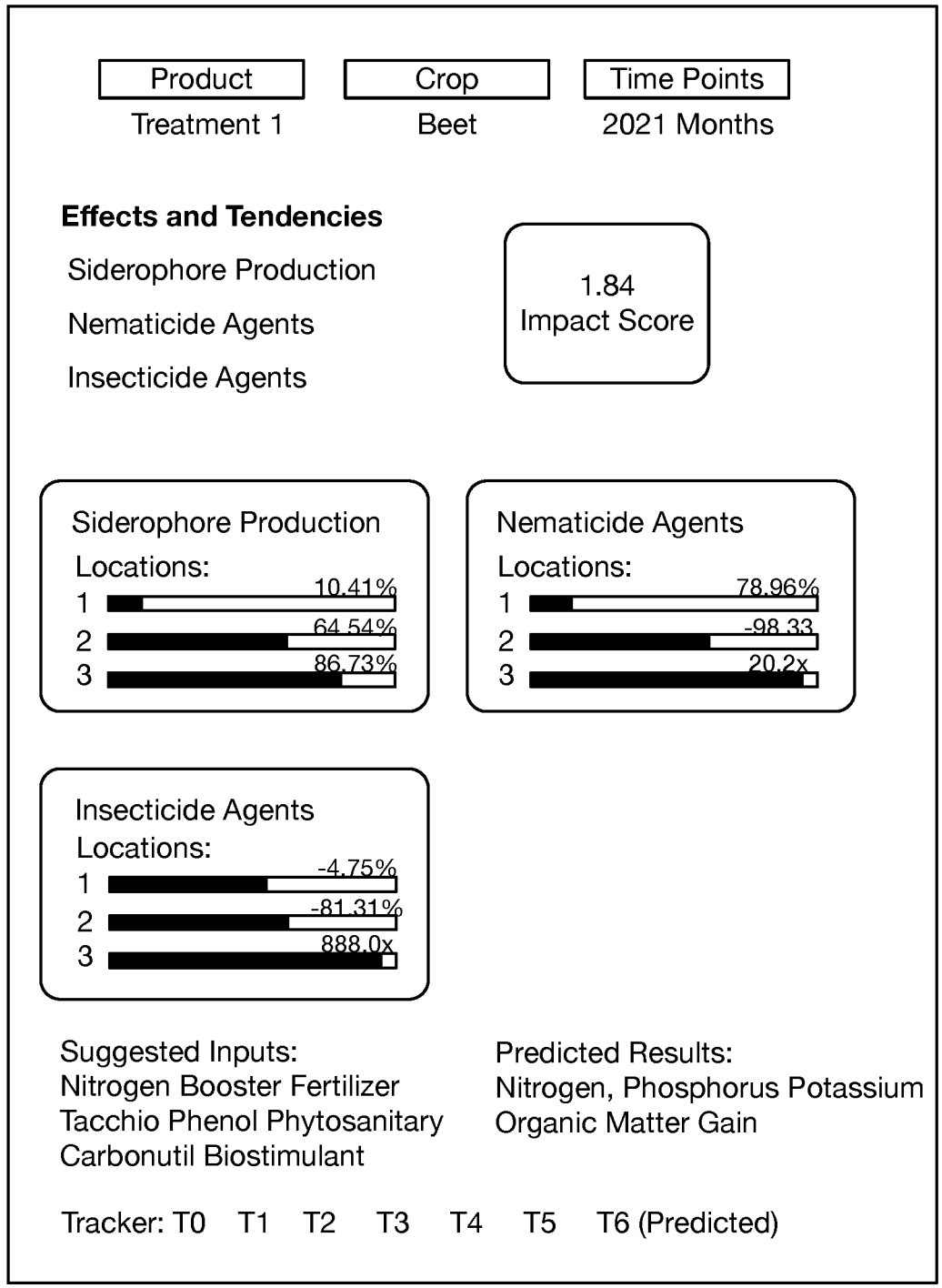
FIG. 6 depicts an example output of embodiments of the system(s) and method(s) described.

In generating recommended actions, Step S160 can include returning notifications or other information derived from the analyses and other outputs of described method steps in a visual format, in an audio format, in a haptic format, and/or in any other suitable observable format, to a manager, operator, and/or other entity associated with the agriculture site(s) being assessed. As such, variations of Block S160 can include generating digital objects (e.g., in visual data formats, in audio data formats, in haptic data formats) or instructions for generating digital objects, in communication with client devices (e.g., mobile devices or other devices that are associated with a manager, operator, and/or other entity associated with the agriculture site(s)), where the client devices include visual output components (e.g., a display), audio output components (e.g., speaker), haptic output components (e.g., vibrators), and/or any other suitable components. Client devices can also include input components (e.g., keypads, touch displays, microphones, joysticks, mice, etc.) such that the managers, operators, or other entities associated with the agriculture site(s) can communicate inputs (e.g., commands) related to the generated analyses. In an example shown in FIG. 6, executing the action can include returning a report characterizing effects of a treatment associated with at least one of the first treatment state and the second treatment state upon siderophore production, nematicide agent presence, and insecticide agent presence.

Additionally or alternatively, generating recommended actions can include generating control instructions for apparatus (e.g., machinery, robotic apparatus configured to traverse an agricultural site, other apparatus) configured to execute computer-readable instructions for management of the agriculture site(s). In variations, control instructions can involve instructions for controlling operation modes of one or more of: watering subsystems (e.g., in relation to water distribution through conduits and/or sprinklers to the agriculture site(s)); product delivery subsystems in communication with watering subsystems (e.g., delivery subsystems in communication with watering subsystems through fluidic components, valves, etc.); robotic crop handling subsystems (e.g., in relation to removal of pathogen-affected crop portions); robotic crop picking subsystems (e.g., in relation to automated harvesting at optimal time periods in relation to improving production, in relation to efficiency of new production generation post-harvesting, in relation to minimization of wasted product, etc.); robotic nutrient delivery or pesticide delivery subsystems (e.g., in relation to initiating delivery, in relation to stopping delivery, in relation to adjusting frequency of delivery, in relation to adjusting delivery dosages, etc.); greenhouse subsystems; temperature control subsystems (e.g., in relation to modes for controlling environmental temperature of the agriculture site, etc.); light control subsystems (e.g., in relation to modes for controlling environmental light of the agriculture site, in relation to transitioning between on and off states, in relation to light spectrum delivered, etc.); gas environment subsystems (e.g., in relation to modes for controlling environmental gas composition of the agriculture site, etc.); humidity control subsystems (e.g., in relation to modes for controlling environmental humidity levels of the agriculture site, etc.); pressure control subsystems (e.g., in relation to modes for controlling environmental pressure of the agriculture site, etc.); and other suitable subsystem(s) of the agriculture site(s). Additionally or alternatively, Block S150 can include generation of control instructions for automated vehicle platforms associated with controlling vehicles associated with the agriculture site(s), with respect to surveying, management, and/or other operation modes.

In examples, instructions for controlling operation modes of watering subsystems (e.g., in relation to water distribution through conduits and/or sprinklers to the agriculture site(s)) can be automatically executed in response to detected states of undesired watering levels based upon model outputs from other steps of the method. As such, controlling operation modes can include transitioning the watering subsystems between various states of flow, on-off states, etc. Control can be modulated in relation to constraints associated with water usage (e.g., times of drought, in relation to water usage incentives, etc.).

In examples, instructions for controlling operation modes of product delivery subsystems (e.g., delivery subsystems in communication with watering subsystems through fluidic components, valves, etc.) can be automatically executed in response to detected states of undesired supplement levels based upon model outputs from other steps of the method. As such, controlling operation modes can include transitioning the delivery subsystems between various states of product dosage, flow rates, on-off states, etc.

In examples, instructions for controlling operation modes of robotic crop handling subsystems (e.g., in relation to removal of pathogen-affected crop portions), robotic crop picking subsystems (e.g., in relation to automated harvesting at optimal time periods in relation to improving production, in relation to efficiency of new production generation post-harvesting, in relation to minimization of wasted product, etc.), robotic nutrient delivery or pesticide delivery subsystems (e.g., in relation to initiating delivery, in relation to stopping delivery, in relation to adjusting frequency of delivery, in relation to adjusting delivery dosages, etc.), and/or other robotic subsystems can be automatically executed in response to detected states of harvesting time, pathogen detection, nutrient states, pest presence, and/or other factors based upon model outputs from other steps of the method. As such, controlling operation modes can include transitioning the robotic subsystems between various states of actuation.

In examples, instructions for controlling operation modes of greenhouse subsystems, temperature control subsystems (e.g., in relation to modes for controlling environmental temperature of the agriculture site, etc.), light control subsystems (e.g., in relation to modes for controlling environmental light of the agriculture site, in relation to transitioning between on and off states, in relation to light spectrum delivered, etc.), gas environment subsystems (e.g., in relation to modes for controlling environmental gas composition of the agriculture site, etc.), humidity control subsystems (e.g., in relation to modes for controlling environmental humidity levels of the agriculture site, etc.), pressure control subsystems (e.g., in relation to modes for controlling environmental pressure of the agriculture site, etc.), and/or other environmental control subsystems can be automatically executed in response to detected states of environmental conditions suited to or unsuited for desired outcomes, and/or other factors based upon model outputs from other steps of the method. As such, controlling operation modes can include transitioning the environmental control subsystems between various states of temperature control, light control, gas control, humidity control, pressure control, and/or other environmental control. Control can be modulated in relation to constraints associated with power usage (e.g., times of peak demand, in relation to demand incentives, etc.).

Additionally or alternatively, step S160 can include generation of control instructions for automated vehicle platforms associated with controlling vehicles associated with the agriculture site(s), with respect to surveying, management, and/or other operation modes.

Block S160 can include or be associated with executing the recommended action through electronic communication with one or more subsystems described above, which functions to automatically execute recommended actions in order to reduce operator workload in relation to agriculture site management. Executed actions can include or be associated with one or more of: maintaining a status of an agriculture site by providing guidance for maintaining current management statuses and/or products used; responding to an issue detected at the agriculture site(s) being assessed (e.g., in relation to pathogen presence, in relation to detrimental microorganism presence, in relation to correcting a perturbation, in relation to adjusting application of a product at the agriculture site, implementing protective measures against environmental effects, etc.); responding to or otherwise correcting other undesired statuses at one or more agriculture sites being monitored; maintaining or improving desired statuses at one or more agriculture sites being monitored (e.g., in relation to biocontrol microorganism presence, in relation to stress tolerance microorganism presence, in relation to plant growth promoter microorganism presence, in relation to nutrient metabolizing microorganism presence, etc.); providing information regarding site characteristics to a manager/operator/other entity associated with the agriculture site(s); performing decision-making guidance (e.g., in relation to analyses indicative of sustainability of practices, in relation to long term effects of use of one or more products, etc.); and performing other suitable actions, as described above in embodiments, variations, and examples of agriculture site management control and notification/report delivery. Step S160 can further implement boundary conditions in relation to cost (e.g., cost optimization) of options for adjusting usage of agricultural inputs (e.g., stimulants, inoculants, etc.) and/or management practices, as well as estimated impacts on the environment (e.g., in relation to level of carbon sequestration), in order to guide execution of actions. As such, Step S160 can include generating an estimate of carbon sequestration level provided by a candidate action and/or an estimate of cost of a candidate action, and executing the candidate action if the estimate of carbon sequestration level and estimate of cost satisfy respective threshold levels.

Embodiments, variations, and examples of actions are further described in Applications incorporated by reference above.

3. System

Figure 5A:
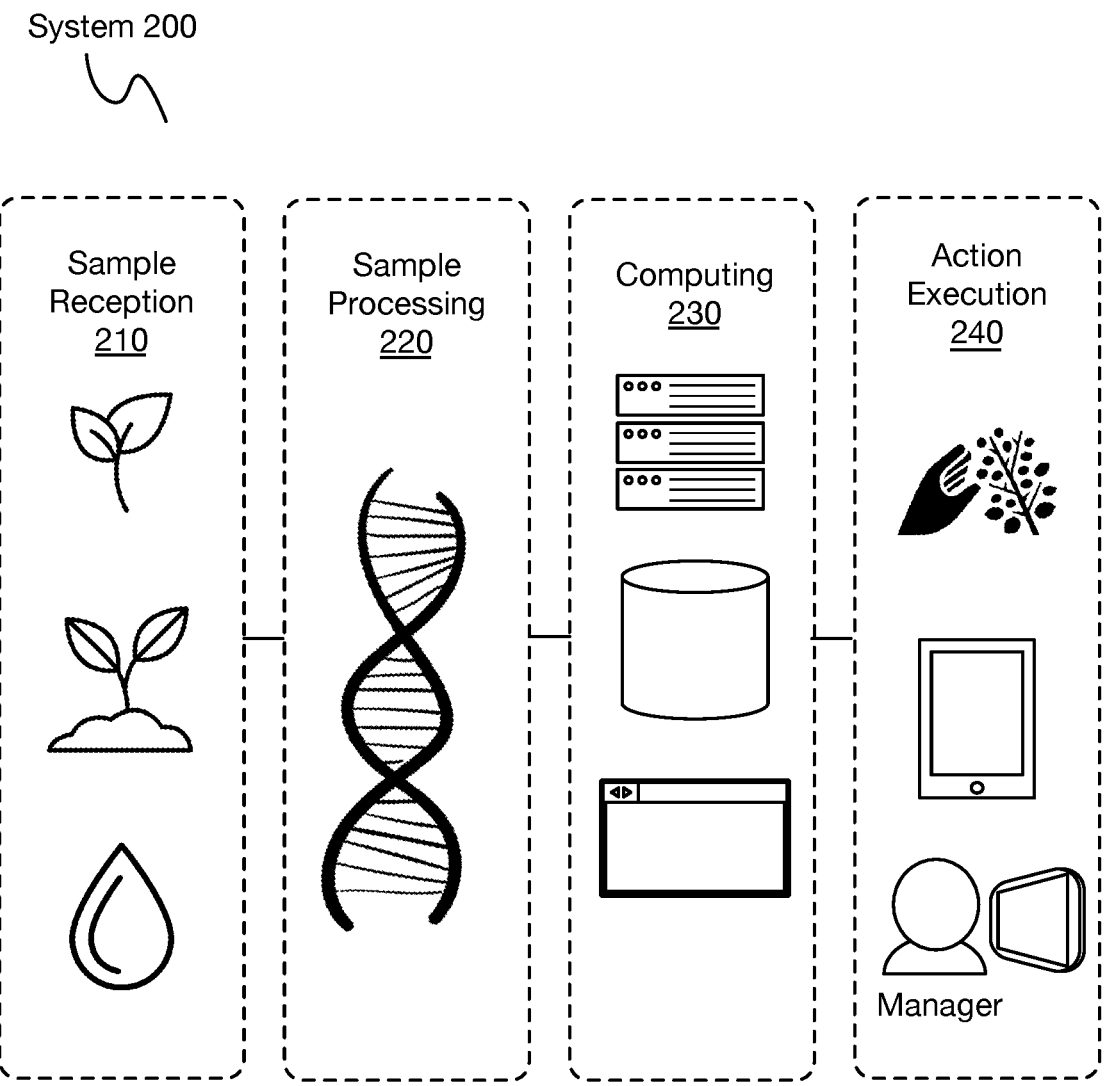
FIGS. 5A and 5B depict an embodiment of a system and respective operation mode structural configurations for assessing agriculture practices and inputs.
Figure 5B:
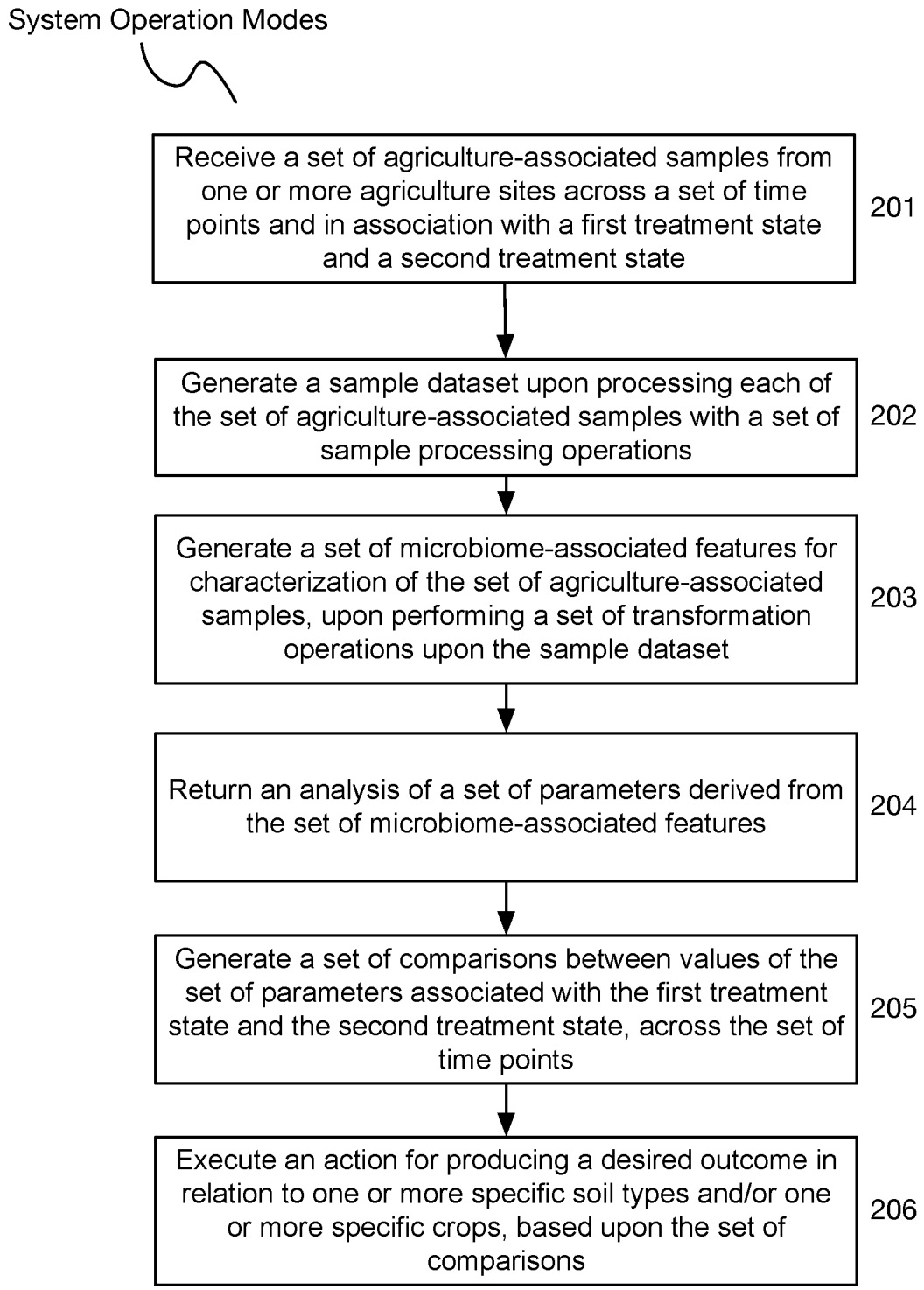

As shown in FIGS. 5A and 5B, a system 200 for characterization and improvement of an agricultural site includes: one or more sample reception subsystems 210; one or more sample processing subsystems 220 in communication with the sample reception subsystems 210; a computing platform 230 comprising one or more processing subsystems comprising non-transitory computer-readable medium comprising instructions stored thereon, that when executed by the processing subsystems perform one or more steps of methods described above; and one or more action execution subsystems 240 configured to execute actions informed by processes of the computing platform 230. In variations, the action execution subsystems 240 can be configured to execute control instructions generated by the computing platform 230, where control instructions can involve instructions for controlling operation modes of one or more of: watering subsystems (e.g., in relation to water distribution through conduits and/or sprinklers to the agriculture site(s)); product delivery subsystems in communication with watering subsystems (e.g., delivery subsystems in communication with watering subsystems through fluidic components, valves, etc.); robotic crop handling subsystems (e.g., in relation to removal of pathogen-affected crop portions); robotic crop picking subsystems (e.g., in relation to automated harvesting at optimal time periods in relation to improving production, in relation to efficiency of new production generation post-harvesting, in relation to minimization of wasted product, etc.); robotic nutrient delivery subsystems (e.g., in relation to initiating delivery, in relation to stopping delivery, in relation to adjusting frequency of delivery, in relation to adjusting delivery dosages, etc.); greenhouse subsystems; temperature control subsystems (e.g., in relation to modes for controlling environmental temperature of the agriculture site, etc.); light control subsystems (e.g., in relation to modes for controlling environmental light of the agriculture site, in relation to transitioning between on and off states, in relation to light spectrum delivered, etc.); gas environment subsystems (e.g., in relation to modes for controlling environmental gas composition of the agriculture site, etc.); humidity control subsystems (e.g., in relation to modes for controlling environmental humidity levels of the agriculture site, etc.); pressure control subsystems (e.g., in relation to modes for controlling environmental pressure of the agriculture site, etc.); and other suitable subsystem(s) of the agriculture site(s).

Embodiments of the system 200 are configured to perform one or more portions of methods described above; as such, embodiments of the system can include non-transitory media storing computer-readable instructions that, when executed by the system 200, perform all or a portion of method steps described above. Furthermore, the system 200 is configured to transition between operation modes with associated structural configurations, where such operation modes include (as shown in FIG. 5B): a first operation mode in which said sample reception subsystems receive a set of agriculture-associated samples from one or more agriculture sites across a set of time points and in association with one of a first treatment state and a second treatment state 201; a second operation mode in which said computing platform generates a sample dataset upon receiving digital objects generated using the sample reception subsystems, upon processing each of the set of agriculture-associated samples with a set of sample processing operations 202; a third operation mode in which said computing platform processes the sample dataset as inputs with first architecture for generating a set of microbiome-associated features for characterization of the set of agriculture-associated samples, upon performing a set of transformation operations upon the sample dataset 203; a fourth operation mode in which said computing platform processes the set of microbiome-associated features with second architecture for returning an analysis of a set of parameters derived from the set of microbiome-associated features 204; a fifth operation mode in which said computing platform processes the analysis with third architecture for generating a set of comparisons between values of the set of parameters associated with the first treatment state and the second treatment state, across the set of time points 205; and a sixth operation mode in which said action execution subsystems execute control instructions for an action for producing a desired outcome in relation to one or more specific soil types and one or more specific crops associated with the one or more agriculture sites, based upon the set of comparisons 206. However, variations of the system 200 can be configured to perform other suitable methods.

4. Conclusions

Embodiments of the invention(s) can include every combination and permutation of the various system components and the various method processes, including any variants (e.g., embodiments, variations, examples, specific examples, figures, etc.), where portions of embodiments of the methods and/or processes described herein can be performed asynchronously (e.g., sequentially), concurrently (e.g., in parallel), or in any other suitable order by and/or using one or more instances, elements, components of, and/or other aspects of the system and/or other entities described herein.

Any of the variants described herein (e.g., embodiments, variations, examples, specific examples, figures, etc.) and/or any portion of the variants described herein can be additionally or alternatively combined, aggregated, excluded, used, performed serially, performed in parallel, and/or otherwise applied.

Portions of embodiments of the methods and/or systems can be embodied and/or implemented at least in part as a machine configured to receive a computer-readable medium storing computer-readable instructions. The instructions can be executed by computer-executable components that can be integrated with embodiments of the system. The computer-readable medium can be stored on any suitable computer-readable media such as RAMs, ROMs, flash memory, EEPROMs, optical devices (CD or DVD), hard drives, floppy drives, or any suitable device. The computer-executable component can be a general or application specific processor, but any suitable dedicated hardware or hardware/firmware combination device can alternatively or additionally execute the instructions.

As a person skilled in the art will recognize from the previous detailed description and from the figures and claims, modifications and changes can be made to embodiments of the methods, systems, and/or variants without departing from the scope defined in the claims. Variants described herein are not meant to be restrictive. Certain features included in the drawings may be exaggerated in size, and other features may be omitted for clarity and should not be restrictive. The figures are not necessarily to scale. The absolute or relative dimensions or proportions may vary. Section titles herein are used for organizational convenience and are not meant to be restrictive. The description of any variant is not necessarily limited to any section of this specification.

What is claimed is:

1. A method comprising:
   receiving a set of agriculture-associated samples from one or more agriculture sites across a set of time points and in association with one of a first treatment state and a second treatment state;
   generating a sample dataset upon processing each of the set of agriculture-associated samples with a set of sample processing operations;
   generating a set of microbiome-associated features for characterization of the set of agriculture-associated samples, upon performing a set of transformation operations upon the sample dataset, wherein the set of microbiome-associated features comprises a set of taxonomic annotations, a set of functional annotations, a set of ecological indices and a set of network properties;
   returning an analysis of a set of parameters derived from the set of microbiome-associated features, wherein the set of parameters comprises a set of agronomic indices, wherein the set of agronomic indices comprises a first category of biosustainability indices comprising a resistance index determined from transitivity of a network and presence of biocontrol species represented in the set of agriculture-associated samples, a second category of health indices comprising a phytohormone-producing species metric characterizing relative abundance of microorganisms that produce phytohormones, and a third category of nutrition indices characterizing physicochemical properties of the set of agriculture-associated samples;
   generating a set of comparisons between values of the set of parameters associated with the first treatment state and the second treatment state, across the set of time points; and
   executing an action for producing a desired outcome in relation to one or more specific soil types and one or more specific crops associated with the one or more agriculture sites, based upon the set of comparisons.

2. The method of claim 1, wherein at least one of the first treatment state and the second treatment state comprises a soil amendment, a biostimulant, a chemical fertilizer, and a biofertilizer.

3. The method of claim 1, wherein at least one of the first treatment state and the second treatment state comprises a management practice comprising one of a conventional management practice, a regenerative management practice, an organic management practice, and a biodynamic management practice.

4. The method of claim 1, wherein generating the set of microbiome-associated features comprises:
from the sample dataset, constructing a metanetwork representation of the one or more agriculture sites, wherein generating the metanetwork representation comprises performing a network inference operation involving:
determination of relative abundances of taxa represented in the sample dataset, determination of a subset of taxa having relative abundance greater than an abundance threshold and prevalence greater than a prevalence threshold, determination of a set of correlations between taxon pairs of the subset of taxa having co-occurrence values greater than a co-occurrence threshold, and constructing the metanetwork representation from the set of correlations.

5. The method of claim 4, wherein generating the set of microbiome-associated features comprises:
generating, from the metanetwork representation, a set of local networks capturing taxa represented at and corresponding to the set of agriculture-associated samples, and
generating, for each of the set of local networks, one or more of the set of network properties.

6. The method of claim 5, wherein each of the set of local networks comprises a set of nodes and edges, and wherein the set of network properties comprises:
a connected components property characterizing subnetworks in which two nodes are connected by edges of the set of nodes and edges, wherein said two nodes lack connection to any other node of the set of nodes and edges;
a clustering coefficient characterizing degree to which nodes of the set of nodes and edges cluster together;
an average path length property characterizing a mean of a minimal number of edges needed to connect any two nodes of the set of nodes and edges;
a similarity property characterizing similarity of local networks to metanetworks;
an assortativity measure characterizing similarity of nodes to neighboring nodes;
a centrality property describing connectedness of nodes;
a centralization property describing ratios between observed centrality and theoretical maximum centrality;
an eigenvalue property describing a largest eigenvalue of a matrix representation of at least one local network;
an articulation property describing a number of nodes that would fragment at least one local network upon deletion; and
a clique property that describes a number of cliques which cannot be generalized to larger cliques, wherein a clique is a group of nodes connected to all other nodes in the clique.

7. The method of claim 5, wherein at least one of constructing the metanetwork representation and generating the set of local networks comprises performing an inter-kingdom network inference operation with a combination of 16S components and ITS components from the sample dataset.

8. The method of claim 1, wherein the set of taxonomic annotations comprises annotations derived from: operational taxonomic units (OTUs), amplicon-sequence variants (ASVs), taxonomic quantification values generated upon addition of a synthetic spike to the set of samples, diversity metrics capturing alpha and beta diversity of taxonomic groups, and abundance parameters comprising bacterial abundance and fungal abundance parameters.

9. The method of claim 1, wherein the set of functional annotations comprises annotations derived from:
nutrient metabolic pathways generated from predicted metagenomic functional factors;
plant growth promoter-associated factors comprising features associated with salt tolerance, heavy metal solubilization, indoleacetic acid production, cytokinin production, gibberellin production, ACC deaminase, exopolysaccharide production, abscisic acid, salicylic acid, and siderophore production;
biocontrol species factors comprising features associated with fungicide biocontrol agents, bactericide biocontrol agents, nematicide biocontrol agents, and insecticide biocontrol agents;
functional diversity metrics;
major nutrient-associated functions comprising: carbon pathways, nitrogen pathways, phosphorus pathways, and potassium pathways; and
minor nutrient-associated functions comprising: iron pathways, zinc pathways, manganese pathways, sulfur pathways, calcium pathways, copper pathways, chlorine pathways, and magnesium pathways.

10. The method of claim 1, wherein the set of ecological indices further comprises:
disease-risk indices associated with one or more of: rot, scab, wilt, blight, scurf, canker, wart, dot, spot, pit, blotch, rust, gangrene, mold, leak, mildew, and smut;
an impact parameter representing changes in co-occurrence and co-exclusion of bacterial and fungal organisms represented in the sample dataset; and
a sustainable productivity index generated from a combination of network properties and principal components of taxonomy generated from the sample dataset.

11. The method of claim 1, wherein the set of agronomic indices comprises: generating a biosustainability index, and wherein the biosustainability index is derived from a biodiversity value representing species richness, a functionality value representing metagenomic functions, and a resistance value representing stress adaptation of communities represented in the sample dataset.

12. The method of claim 1, wherein the second category of health indices comprises a health index is derived from a healthiness value associated with detected pathogens, a biocontrol value representing capability of preventing pathogenic species effects at the agriculture site, and a stress value representing metabolites associated with stress withstanding.

13. The method of claim 1, wherein the third category of nutrition indices comprises a nutrition index is derived from values of nutrient dynamic parameters represented in the sample dataset.

14. The method of claim 1, wherein generating the set of comparisons between values of the set of parameters associated with the first treatment state and the second treatment state comprises generating distances between centroids of diversity values corresponding to microbiome composition of bacteria and fungi represented in the set of agriculture-associated samples, across the set of time points.

15. The method of claim 1, wherein generating the set of comparisons between values of the set of parameters comprises generating a comparison between bioavailability of nutrients at a first time point and a second time point of the set of time points.

16. The method of claim 1, wherein executing the action comprises applying of one or more of: a biofertilizer, a biostimulant, a biocontrol agent, an agent for hormone production, an agent configured to promote stress adaptation, and a nutrient at the agriculture site.

17. The method of claim 1, wherein executing the action comprises returning a report characterizing effects of a treatment associated with at least one of the first treatment state and the second treatment state upon siderophore production, nematicide agent presence, and insecticide agent presence.

18. The method of claim 1, further comprising: generating an estimate of carbon sequestration level provided by a candidate action and an estimate of cost of a candidate action, and wherein executing the action comprises executing the candidate action if the estimate of carbon sequestration level and estimate of cost satisfy respective threshold levels.

* * * * *